United States Patent
Joly et al.

(10) Patent No.: US 9,414,996 B2
(45) Date of Patent: Aug. 16, 2016

(54) DENTAL COMPOSITIONS COMPRISING ADDITION-FRAGMENTATION AGENTS

(71) Applicant: 3M INNOVATIVE PROPERTIES COMPANY, St. Paul, MN (US)

(72) Inventors: Guy D. Joly, Shoreview, MN (US); Ahmed S. Abuelyaman, Woodbury, MN (US); Ann R. Fornof, St. Paul, MN (US); Bradley D. Craig, Lake Elmo, MN (US); Larry R. Krepski, White Bear Lake, MN (US); William H. Moser, Edina, MN (US); Serkan Yurt, St. Paul, MN (US); Joel D. Oxman, Minneapolis, MN (US); Afshin Falsafi, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 14/437,200

(22) PCT Filed: Oct. 31, 2013

(86) PCT No.: PCT/US2013/067638
§ 371 (c)(1),
(2) Date: Apr. 21, 2015

(87) PCT Pub. No.: WO2014/074373
PCT Pub. Date: May 15, 2014

(65) Prior Publication Data
US 2015/0283039 A1    Oct. 8, 2015

Related U.S. Application Data

(60) Provisional application No. 61/725,077, filed on Nov. 12, 2012.

(51) Int. Cl.
*A61K 6/083* (2006.01)
*A61K 6/00* (2006.01)
*C09J 133/14* (2006.01)

(52) U.S. Cl.
CPC ............... *A61K 6/083* (2013.01); *A61K 6/0023* (2013.01); *A61K 6/0088* (2013.01); *A61K 6/0835* (2013.01); *C09J 133/14* (2013.01)

(58) Field of Classification Search
None
See application file for complete search history.

(56) References Cited

U.S. PATENT DOCUMENTS

| | | |
|---|---|---|
| 2,801,185 A | 7/1957 | Iler |
| 4,503,169 A | 3/1985 | Randklev |
| 4,522,958 A | 6/1985 | Das |
| 4,547,323 A | 10/1985 | Carlson |
| 4,886,861 A | 12/1989 | Janowicz |
| 5,130,347 A | 7/1992 | Mitra |
| 5,154,762 A | 10/1992 | Mitra |
| 5,324,879 A | 6/1994 | Hawthorne |
| 5,501,727 A | 3/1996 | Wang |
| 5,506,279 A | 4/1996 | Babu |
| 5,545,676 A | 8/1996 | Palazzotto |
| 5,925,715 A | 7/1999 | Mitra |
| 5,962,550 A | 10/1999 | Akahane |
| 6,126,922 A | 10/2000 | Rozzi |
| 6,153,705 A | 11/2000 | Corpart |
| 6,316,519 B1 | 11/2001 | Berge |
| 6,376,590 B2 | 4/2002 | Kolb |
| 6,387,981 B1 | 5/2002 | Zhang |
| 6,572,693 B1 | 6/2003 | Wu |
| 6,586,483 B2 | 7/2003 | Kolb |
| 6,670,436 B2 | 12/2003 | Burgath |
| 6,730,156 B1 | 5/2004 | Windisch |
| 6,747,111 B2 | 6/2004 | Chiefari |
| 6,794,520 B1 | 9/2004 | Moszner |
| 6,812,291 B1 | 11/2004 | Corpart |
| 7,090,721 B2 | 8/2006 | Craig |
| 7,090,722 B2 | 8/2006 | Budd |
| 7,156,911 B2 | 1/2007 | Kangas |
| 7,241,437 B2 | 7/2007 | Davidson |
| 7,250,479 B2 | 7/2007 | Le |
| 7,429,422 B2 | 9/2008 | Davidson |
| 7,649,029 B2 | 1/2010 | Kolb |
| 7,674,850 B2 | 3/2010 | Karim |
| 7,838,110 B2 | 11/2010 | Zhu |
| 7,888,400 B2 | 2/2011 | Abuelyaman |
| 7,943,680 B2 | 5/2011 | Bowman |
| 2005/0017966 A1 | 1/2005 | Engl |
| 2005/0256223 A1 | 11/2005 | Kolb |
| 2006/0009574 A1 | 1/2006 | Aert |
| 2008/0076848 A1 | 3/2008 | Jin |
| 2009/0030110 A1 | 1/2009 | Klee |
| 2010/0021869 A1 | 1/2010 | Abuelyaman |
| 2010/0311858 A1 | 12/2010 | Holmes |

(Continued)

FOREIGN PATENT DOCUMENTS

| WO | WO 01-30305 | 5/2001 |
|---|---|---|
| WO | WO 01-30307 | 5/2001 |

(Continued)

OTHER PUBLICATIONS

Adamson, "Aminoalkyl Tertiary Carbinols," Journal of the Chemical Society, 1949, pp. S144-S155.
Cara, "Influence of Bis-GMA Derivative Monomer-Based Particulate Composite Resins on the Cuspal Deformation and Microleakage of Restored Teeth", Particulate Science and Technology, 2010, vol. 28, pp. 191-206.
Enikolopyan, "Catalyzed Chain Transfer to Monomer in Free Radical Polymerization", Journal of Polymer Science: Polymer Chemistry Edition, 1981, vol. 19, pp. 879-889.
Hutson, "Chain Transfer Activity of ω-Unsaturated Methacrylic Oligomers in Polymerizations of Methacrylic Monomers", Macromolecules, 2004, vol. 37, pp. 4441-4452.
Kloxin, "Stress Relaxation via Addition-Fragmentation Chain Transfer in a Thiol-ene Photopolymerization", Macromolecules, 2009, vol. 42, pp. 2551-2556.
Matijevic, "Surface and Colloid Science", 1973, vol. 6, pp. 23-29.

(Continued)

*Primary Examiner* — Robert S Loewe
(74) *Attorney, Agent, or Firm* — Kent S. Kokko

(57) ABSTRACT

A curable dental composition comprising an addition-fragmentation agent and a curable dental resin is disclosed.

19 Claims, No Drawings

(56) References Cited

U.S. PATENT DOCUMENTS

| | | |
|---|---|---|
| 2011/0041736 A1 | 2/2011 | Gartner |
| 2011/0196062 A1 | 8/2011 | Craig |
| 2012/0016052 A1 | 1/2012 | Bowman |
| 2012/0208965 A1 | 8/2012 | Joly |

FOREIGN PATENT DOCUMENTS

| | | |
|---|---|---|
| WO | WO 03-063804 | 8/2003 |
| WO | WO 2009-091551 | 7/2009 |
| WO | WO 2011-126647 | 10/2011 |
| WO | WO 2012-003136 | 1/2012 |
| WO | WO 2012-112321 | 8/2012 |
| WO | WO 2012-112350 | 8/2012 |
| WO | WO 2013-028397 | 2/2013 |
| WO | WO 2013-028401 | 2/2013 |
| WO | WO 2014-074427 | 5/2014 |

OTHER PUBLICATIONS

Meijs, "Preparation of Controlled Molecular Weight, Olefin-Terminated Polymers by Free Radical Methods. Chain Transfer Using Allylic Sulfides", Macromolecules, 1988, vol. 21, No. 10, pp. 3122-3124.

Moad, "Radical addition-fragmentation chemistry in polymer synthesis", Polymer, 2008, vol. 49, pp. 1079-1131.

Temel, "Photopolymerization and photophysical properties of amine linked benzophenone photoinitiator for free radical polymerization", Journal of Photochemistry and Photobiology A: Chemistry, 2011, vol. 219, pp. 26-31.

International Search Report for PCT International Application No. PCT/US2013/067638, mailed on Mar. 4, 2014, 4pgs.

DENTAL COMPOSITIONS COMPRISING ADDITION-FRAGMENTATION AGENTS

CROSS REFERENCE TO RELATED APPLICATIONS

This application is a national stage filing under 35 U.S.C. 371 of PCT/US2013/067638, filed Oct. 31, 2013, which claims priority to Provisional Application No. 61/725,077, filed Nov. 12, 2012, the disclosure of which is incorporated by reference in its/their entirety herein.

BACKGROUND

Curable polymeric materials are used in a wide variety of dental applications, including restoratives, cements, adhesives, and the like. Often, such materials shrink upon curing. This is particularly problematic when the material is in a constrained environment, as in a dental filling or restorative, for example. Dimensional changes upon shrinkage while in a constrained environment can generate a strain within the material that is typically converted into a stress on the surrounding environment (e.g., tooth). Such forces can result in interfacial failures between the tooth and the polymeric material resulting in a physical gap and subsequent microleakage into the tooth cavity. Alternatively, such forces can lead to fractures within the tooth and/or the composite.

Generally, conventional processes of curing polymeric dental materials involve a composite held in place on an oral surface with an adhesive and involve curing the adhesive and then subsequently curing the composite material. More specifically, conventional methods utilize one or more of the following steps: surface treatment of the tooth (e.g., etching, priming), application of a curable adhesive to the tooth surface, curing of the adhesive, placement of a composite material (e.g., restorative) on the cured adhesive, and curing of the composite material. There is a need for dental materials, e.g., dental adhesives and dental composites, that reduce the amount of stress placed on the dental material and the surrounding environment during or after curing.

SUMMARY

Although various curable dental compositions have been described, industry would find advantage in compositions having improved properties such as reduced stress deflection and/or reduced shrinkage while maintaining sufficient mechanical properties and depth of cure.

In some embodiments, the present disclosure provides curable dental compositions that are self-adhesive, and require no separate etchant or etching step.

The restoration of dental structures including caries, decayed dentin or decayed enamel, is often accomplished by the sequential application of a dental adhesive and then a dental material (e.g., a restorative material) to the relevant dental structures. Similarly, adhesives are also used in the bonding of dental materials (e.g., orthodontic appliances, generally utilizing an orthodontic adhesive) to a dental structure. Often various pretreatment processes are used to promote the bonding of dental adhesives to dentin or enamel. Typically, such pretreatment steps include etching, for example, using inorganic or organic acids, followed by priming to improve the bonding between the tooth structure and the overlying adhesive.

Whether for application of dental restoratives (e.g., cured or uncured composites such as resin-modified glass ionomers, etc.; fillings; sealants; inlays; onlays; crowns; bridges; etc.) or orthodontic appliances to a dental structure surface, the etchants, primers, and adhesives are typically applied in a step-wise fashion. One or more rinsing and drying steps may be used. As a result, dental restoration and the application of orthodontic appliances typically involve multi-step procedures.

To simplify conventional restorative and/or orthodontic procedures, for example, it would be desirable to provide a single composition that accomplishes both etching and priming. Thus, there is a need for a self-etching primer, particularly a self-etching dental primer, for improved bonding of an adhesive (e.g., a dental adhesive) to a substrate surface (e.g., dental structure, such as dentin, enamel, bone, or other hard tissue) and that could eliminate the conventional post-etching rinsing and drying steps. Furthermore, there is still a need for new compositions that can serve as self-etching adhesives, i.e., dental compositions with priming and etching properties that can be applied in a single pretreatment step. In yet other dental and orthodontic procedures, there is a need for restorative compositions (e.g., filling materials and orthodontic adhesives) that can serve as self-adhesive compositions (preferably i.e., one-part, shelf-stable compositions) that can bond to an untreated dental structure (i.e., a structure not pretreated with an etchant, primer, or bonding agent). Preferred embodiments of the present disclosure meet these needs.

As used herein, "dental composition" refers to a material, optionally comprising filler, capable of adhering or being bonded to an oral surface. A curable dental composition can be used to bond a dental article to a tooth structure, form a coating (e.g., a sealant or varnish) on a tooth surface, be used as a restorative that is placed directly into the mouth and cured in-situ, or alternatively be used to fabricate a prosthesis outside the mouth that is subsequently adhered within the mouth.

Curable dental compositions include, for example, adhesives (e.g., dental and/or orthodontic adhesives), cements (e.g., resin-modified glass ionomer cements, and/or orthodontic cements), primers (e.g., orthodontic primers), liners (applied to the base of a cavity to reduce tooth sensitivity), coatings such as sealants (e.g., pit and fissure), and varnishes; and resin restoratives (also referred to as direct composites) such as dental fillings, as well as crowns, bridges, and articles for dental implants. Highly filled dental compositions are also used for mill blanks, from which a crown may be milled. A composite is a highly filled paste designed to be suitable for filling substantial defects in tooth structure. Dental cements are somewhat less filled and less viscous materials than composites, and typically act as a bonding agent for additional materials, such as inlays, onlays and the like, or act as the filling material itself if applied and cured in layers. Dental cements are also used for permanently bonding dental restorations such as a crown or bridge to a tooth surface or an implant abutment.

As used herein:

"dental article" refers to an article that can be adhered (e.g., bonded) to a tooth structure or dental implant. Dental articles include, for example, crowns, bridges, veneers, inlays, onlays, fillings, orthodontic appliances and devices.

"orthodontic appliance" refers to any device intended to be bonded to a tooth structure, including, but not limited to, orthodontic brackets, buccal tubes, lingual retainers, orthodontic bands, bite openers, buttons, and cleats. The appliance has a base for receiving adhesive and it can be a flange made of metal, plastic, ceramic, or combinations thereof. Alternatively, the base can be a custom base formed from cured adhesive layer(s) (i.e. single or multi-layer adhesives).

"oral surface" refers to a soft or hard surface in the oral environment. Hard surfaces typically include tooth structure including, for example, natural and artificial tooth surfaces, bone, and the like.

"curable" is descriptive of a material or composition that can be polymerized or crosslinked by a free-radical means such as by irradiating with actinic irradiation to induce polymerization and/or crosslinking; "hardened" refers to a material or composition that has been cured (e.g., polymerized or crosslinked).

"initiator" refers to something that initiates curing of a resin. An initiator may include, for example, a polymerization initiator system, a photoinitiator system, a thermal initiator and/or a redox initiator system.

"self-etching" composition refers to a composition that bonds to a dental structure surface without pretreating the dental structure surface with an etchant. Preferably, a self-etching composition can also function as a self-primer wherein no separate etchant or primer are used.

a "self-adhesive" composition refers to a composition that is capable of bonding to a dental structure surface without pretreating the dental structure surface with a primer or bonding agent. Preferably, a self-adhesive composition is also a self-etching composition wherein no separate etchant is used.

a "dental structure surface" refers to tooth structures (e.g., enamel, dentin, and cementum) and bone.

an "uncut" dental structure surface refers to a dental structure surface that has not been prepared by cutting, grinding, drilling, etc.

an "untreated" dental structure surface refers to a tooth or bone surface that has not been treated with an etchant, primer, or bonding agent prior to application of a self-etching adhesive or a self-adhesive composition of the present invention.

an "unetched" dental structure surface refers to a tooth or bone surface that has not been treated with an etchant prior to application of a self-etching adhesive or a self-adhesive composition of the present invention.

"(meth)acrylate" is a shorthand reference to acrylate, methacrylate, or combinations thereof "(meth)acrylic" is a shorthand reference to acrylic, methacrylic, or combinations thereof and "(meth)acryl" is a shorthand reference to acryl, methacryl, or combinations thereof.

"acryloyl" is used in a generic sense and mean not only derivatives of acrylic acid, but also amine, and alcohol derivatives, respectively;

"(meth)acryloyl" includes both acryloyl and methacryloyl groups; i.e. is inclusive of both esters and amides.

"alkyl" includes straight-chained, branched, and cycloalkyl groups and includes both unsubstituted and substituted alkyl groups. Unless otherwise indicated, the alkyl groups typically contain from 1 to 20 carbon atoms. Examples of "alkyl" as used herein include, but are not limited to, methyl, ethyl, n-propyl, n-butyl, n-pentyl, isobutyl, t-butyl, isopropyl, n-octyl, n-heptyl, ethylhexyl, cyclopentyl, cyclohexyl, cycloheptyl, adamantyl, and norbornyl, and the like. Unless otherwise noted, alkyl groups may be mono- or polyvalent, i.e monvalent alkyl or polyvalent alkylene.

"heteroalkyl" includes both straight-chained, branched, and cyclic alkyl groups with one or more heteroatoms independently selected from S, O, and N with both unsubstituted and substituted alkyl groups. Unless otherwise indicated, the heteroalkyl groups typically contain from 1 to 20 carbon atoms. "Heteroalkyl" is a subset of "hydrocarbyl containing one or more S, N, O, P, or Si atoms" described below. Examples of "heteroalkyl" as used herein include, but are not limited to, methoxy, ethoxy, propoxy, 3,6-dioxaheptyl, 3-(trimethylsilyl)-propyl, 4-dimethylaminobutyl, and the like.

Unless otherwise noted, heteroalkyl groups may be mono- or polyvalent, i.e. monovalent heteroalkyl or polyvalent heteroalkylene.

"aryl" is an aromatic group containing 5-18 ring atoms and can contain optional fused rings, which may be saturated, unsaturated, or aromatic. Examples of an aryl groups include phenyl, naphthyl, biphenyl, phenanthryl, and anthracyl. Heteroaryl is aryl containing 1-3 heteroatoms such as nitrogen, oxygen, or sulfur and can contain fused rings. Some examples of heteroaryl groups are pyridyl, furanyl, pyrrolyl, thienyl, thiazolyl, oxazolyl, imidazolyl, indolyl, benzofuranyl, and benzthiazolyl. Unless otherwise noted, aryl and heteroaryl groups may be mono- or polyvalent, i.e. monovalent aryl or polyvalent arylene.

"(hetero)hydrocarbyl" is inclusive of hydrocarbyl alkyl and aryl groups, and heterohydrocarbyl heteroalkyl and heteroaryl groups, the later comprising one or more catenary (in-chain) oxygen heteroatoms such as ether or amino groups. Heterohydrocarbyl may optionally contain one or more catenary (in-chain) functional groups including ester, amide, urea, urethane, and carbonate functional groups. Unless otherwise indicated, the non-polymeric (hetero)hydrocarbyl groups typically contain from 1 to 60 carbon atoms. Some examples of such heterohydrocarbyls as used herein include, but are not limited to, methoxy, ethoxy, propoxy, 4-diphenylaminobutyl, 2-(2'-phenoxyethoxy)ethyl, 3,6-dioxaheptyl, 3,6-dioxahexyl-6-phenyl, in addition to those described for "alkyl", "heteroalkyl", "aryl", and "heteroaryl" supra.

"Binding" in the context of surface-binding functional groups refers to the formation of a covalent or ionic bond between the addition-fragmentation agent and the substrate. Binding also includes the etching of the substrate by the surface-binding functional groups, for example the etching of a dental substrate by an acidic group.

DETAILED DESCRIPTION

Presently described are dental compositions, dental articles, and methods of use. The dental composition comprises at least one addition-fragmentation agent having the following functional groups: 1) a labile addition-fragmentation group that can cleave and reform to relieve strain, and 2) at least two surface-binding functional groups that bond with the surface of a substrate (such as a dental structure or article) by forming a covalent or ionic bond. Included in surface-binding groups are those that etch the dental structure or articles, such as the etching of dentin by an acidic functional group.

The addition-fragmentation agent is labile and free-radically cleavable. In some embodiments, the dental compositions are self-adhesive, i.e., do not require a separate step of etching with an acid to promote bonding of the dental composition to a dental structure.

The addition-fragmentation agent is of the general formula

where
AF is an addition-fragmentation group;
$R^1$ and $R^3$ are each independently $Y_p$-Q'-, a (hetero)alkyl group or a (hetero)aryl group with the proviso that the addition-fragmentation agent has at least two Y groups, Q' is a covalent bond or (hetero)hydrocarbyl linking group have a valence of p+1; and Y is a surface-binding organic functional group that associates with a substrate on which the addition-fragmentation agent is disposed.

The addition-fragmentation group "AF" is a labile group that can add, fragment, and add again to the polymer chain to reduce the stress on the growing polymer. Useful addition-fragmentation groups include 1,5-diacyl, 2,2-dimethyl-4-methylene (i.e. derivatives of 2,2-dimethyl-4-methyleneglutaric acid), dithioesters, dithiocarbamates, trithiocarbonates, thiuram disulfides, xanthates vinyl ethers, allyl sulfides, allyl sulfones, allyl sulfoxides, allyl phosphonates, and allyl peroxides.

Suitable addition-fragmentation functionalities or agents for use in the invention also include those functional groups characteristic of conventional reversible addition-fragmentation chain transfer (RAFT) agents. RAFT agents are known to those skilled in the art and are described in G. Moad et al., Radical addition-fragmentation chemistry in polymer synthesis, *Polymer*, Vol. 49, No. 5. (3 Mar. 2008), pp. 1079-1131. Examples of RAFT agents are given in U.S. Pat. No. 6,153, 705, U.S. Pat. No. 7,250,479 (Moad), U.S. Pat. No. 6,812,291 (Corpart et al.), U.S. Pat. No. 6,747,111 (Moad et al.) and U.S. Pat. No. 6,153,705. Allylic sulfide chain transfer groups are described by Meijs et al., Macromolecules, 21(10), 3122-3124, 1998. Suitable addition-fragmentation chain transfer agents include trithiocarbonate or allyl sulfide functionalities.

In certain preferred embodiments, the addition fragmentation group is a 1,5-diacyl, 2,2-dimethyl-4-methylene of the formula:

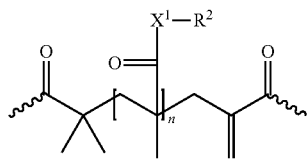

wherein $R^2$ is $Y_p$-Q'-, a (hetero)alkyl group or a (hetero)aryl group;

Q' is a covalent bond or an or a linking group, preferably an organic (hetero)hydrocarbyl linking group having a valence of p+1;

Y is a surface-binding organic functional group;

p is at least 2;

n is 0 or 1.

The addition-fragmentation agents are preferably derivatives of 2,2-dimethyl-4-methyleneglutaric acid of the following formula:

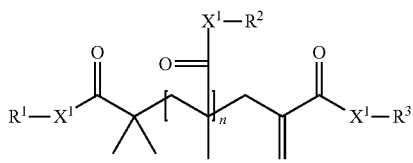

wherein $R^1$, $R^2$ and $R^3$ are each independently Y-Q'-, a (hetero)alkyl group or a (hetero)aryl group with the proviso that at least two of $R^1$, $R^2$ and $R^3$ is $Y_p$-Q'-

Q' is a covalent bond or an or a linking group, preferably an organic (hetero)hydrocarbyl linking group having a valence of p+1;

Y is a surface-binding organic functional group;

p is 1 or 2;

$X^1$ is independently —O— or —$NR^4$—, where $R^4$ is H or $C_1$-$C_4$ alkyl, and n is 0 or 1. It will be further understood that each of $R^1$, $R^2$ and $R^3$ may contain more than one Y-Q'- group.

Addition-fragmentation agents according to Formula I are described in U.S. 2015-0284538 (Joly et al.), incorporated herein by reference.

In a favored embodiment, the addition-fragmentation materials ("AFM") of the formula $R^1$-AF-$R^3$, or those of Formula I may be added to a dental composition comprising at least one ethylenically unsaturated monomer or oligomer. Without intending to be bound by theory, it is surmised that the inclusion of such addition-fragmentation material reduces the polymerization-induced stresses, such as by the mechanism described in U.S. 2015-0284538 (Joly et al.), incorporated herein by reference.

It is believed that the addition-fragmentation agent follows an addition-fragmentation pathway as shown in the following Scheme 1. In this scheme the addition-fragmentation group/ agent of Formula I is shown, where n is 0. In the step 1, a free radical species P. adds to the addition-fragmentation agent. The addition-fragmentation agent then fragments as shown in step 2 to form the stable α-carbonyl tertiary radical and the α,β-unsaturated ester bearing the residue of the free radical species P. This α,β-unsaturated ester can undergo radical addition as shown in step 5. The radical addition may be initiated by an initiator or a polymer radical.

Concurrently the α-carbonyl tertiary radical can initiate polymerization of monomer as shown in step 3. For purposes of illustration, a methacrylate monomer is illustrated. On monomer addition, a methacrylate-terminated radical intermediate is produced. In the presence of the addition-fragmentation agent of Formula 1 (as shown in step 4) both addition and fragmentation, yielding a tertiary radical, occurs. The polymer resulting from step 4 may further fragment and recombine or add additional monomer(s).

Scheme 1.

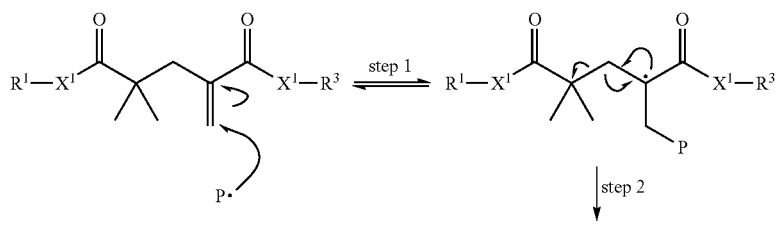

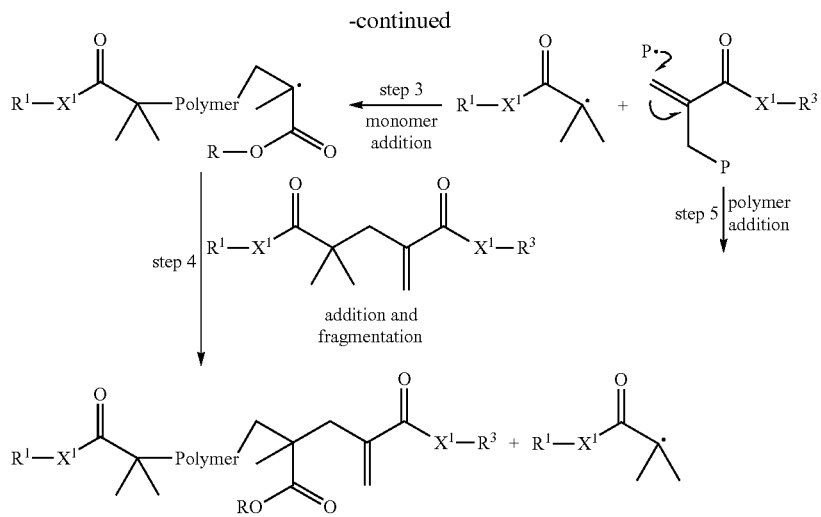

Stress relief could also be a result of attenuated reaction rates (slower cure rates) in the presence of addition-fragmentation agents. The addition of a radical to the addition-fragmentation agent generates a potentially long-lived, tertiary radical (the product of step 1, Scheme 1). This long-lived radical intermediate can revert back to starting materials, add to monomer, or fragment. If fragmentation, retro-addition and monomer addition are slow relative to addition, the intermediate tertiary radical will be relatively long-lived. This long-lived radical intermediate will then act as a radical reservoir, slowing down the overall polymerization process. Attenuated cure rates could serve to delay the transition of a material from a viscous material to an elastic or viscoelastic solid, delaying the gel point. Post-gel shrinkage is a major component in stress development; therefore, delaying the gel point even slightly may lead to stress relief by allowing additional time for material to flow during the curing process. Therefore, even compounds of Formula I may be used to reduce polymerization stress.

With further respect to Formula I, useful Y-Q' groups that may self-adhere or self-etch ($R^1$—$X^1$— groups and optionally $R^2$—X— and $R^3$—$X^1$— groups) include a monophosphate, a phosphonate, a phosphonic acid, a hydroxamic acid, a carboxylic acid, and acetoacetate, an anhydride, an isonitrile group, a silyl, a disulfide, a thiol, an amino, a sulfinic acid, a sulfonic acid, a phosphine, a phenolic (including catechols and 1,2,3-trihydroxy benzene derivatives), or a heterocyclic aromatic group. Of particular interest in dental applications are those Y groups that can bond to, etch, or otherwise associated with a dental structure. Preferred Y groups include a monophosphate, a phosphonate, a phosphonic acid, and a carboxylic acid. The Q' group is selected from —O—, —S—, —N($R^4$)—, —$SO_2$—, —$PO_2$—, —CO—, —OCO—, —$R^6$—, —N($R^4$)—CO—, —N($R^4$)—, —N($R^4$)—CO—O—, —N($R^4$)—CO—$NR^4$—CO—O—$R^6$—, —CO—N($R^4$)—$R^6$—, —$R^6$—CO—O—$R^6$—, —O—$R^6$—, —S—$R^6$—, —$SO_2$—$R^6$—, —$PO_2$—$R^6$—, —CO—$R^6$—, —OCO—$R^6$—, —N($R^4$)—CO—$R^6$—, N($R^4$)—$R^6$—CO—O—, and —N($R^4$)—CO—N($R^4$)—, wherein each $R^4$ is hydrogen, a $C_1$ to $C_4$ alkyl group, or aryl group, each $R^6$ is a (hetero)hydrocarbyl group, as described for the Q group supra.

In another embodiment, Y is a silyl group of the formula —$SiR^7_3$, wherein each $R^7$ group is independently selected from the group of alkoxy, acetoxy, and halide. Such silyl-functional addition fragmentation agents may bond to silica fillers or other ceramic materials of dental devices and compositions.

The total amount of addition-fragmentation agent(s) in the polymerizable resin portion of the unfilled curable dental composition is typically no greater than 15 wt-%. As the concentration of the addition-fragmentation monomer increases, the stress deflection and Watts Shrinkage typically decrease. However, when the amount of addition-fragmentation agent exceeds an optimal amount, mechanical properties such as Diametral tensile strength and/or Barcol hardness, or depth of cure may be insufficient.

The polymerizable resin portion of the curable dental composition described herein comprises at least 0.1 wt-%, of addition-fragmentation agent(s). Generally, the amount of addition-fragmentation agent is from about 0.5 to 10 wt. % of the polymerizable portion of the unfilled dental composition.

The filled curable dental composition described herein typically comprises at least 0.1 wt-%, of addition-fragmentation agent(s). The total amount of addition-fragmentation agent(s) in the filled curable dental composition is typically no greater than 5 wt-%.

Materials with high polymerization stress upon curing generate strain in the tooth structure. One clinical consequence of such stress can be a decrease in the longevity of the restoration. The stress present in the composite passes through the adhesive interface to the tooth structure generating cuspal deflection and cracks in the surrounding dentin and enamel which can lead to postoperative sensitivity as described in R. R. Cara et al, Particulate Science and Technology 28; 191-206 (2010). Preferred (e.g. filled) dental compositions (useful for restorations such as fillings and crowns) described herein typically exhibit a stress deflection of no greater than 2.0, or 1.8, or 1.6, or 1.4, or 1.2 or 1.0 or 0.8 or 0.6 microns.

The compounds of Formula I may be prepared from (meth) acrylate dimers and trimers by substitution, displacement or condensation reactions. The starting (meth)acrylate dimers and trimers may be prepared by free radical addition of a (meth)acryloyl monomer in the presence of a free radical initiator and a cobalt (II) complex catalyst using the process of U.S. Pat. No. 4,547,323, incorporated herein by reference. Alternatively, the (meth)acryloyl dimers and trimers may be prepared using a cobalt chelate complex using the processes of U.S. Pat. No. 4,886,861 (Janowicz) or U.S. Pat. No. 5,324,879 (Hawthorne), incorporated herein by reference. In either process, the reaction mixture can contain a complex mixture of dimers, trimers, higher oligomers and polymers and the desired dimer or trimer can be separated from the mixture by distillation. Such syntheses are further described in U.S. 2015-0284538 (Joly et al.), incorporated herein by reference and the forthcoming examples.

The curable compositions described herein further comprise at least one ethylenically unsaturated resin monomer or oligomer in combination with the addition-fragmentation agent. In some embodiments, such as primers, the ethylenically unsaturated monomer may be monofunctional, having a single (e.g. terminal) ethylenically unsaturated group. In other embodiments, such as dental restorations the ethylenically unsaturated monomer is multifunctional. The phrase "multifunctional ethylenically unsaturated" means that the monomers each comprise at least two ethylenically unsaturated (e.g. free radically) polymerizable groups, such as (meth)acrylate groups.

The amount of curable resin in the dental composition is a function of the desired end use (adhesives, cements, restoratives, etc.) and can be expressed with respect to the (i.e. unfilled) polymerizable resin portion of the dental composition. For favored embodiments, wherein the composition further comprises filler, the concentration of monomer can also be expressed with respect to the total (i.e. filled) composition. When the composition is free of filler, the polymerizable resin portion is the same as the total composition.

In favored embodiments, such ethylenically unsaturated groups of the curable dental resin includes (meth)acryloyl such as (meth)acrylamide and (meth)acrylate. Other ethylenically unsaturated polymerizable groups include vinyl and vinyl ethers. The ethylenically unsaturated terminal polymerizable group(s) is preferably a (meth)acrylate group, particularly for compositions that are hardened by exposure to actinic (e.g. UV and visible) radiation. Further, methacrylate functionality is typically preferred over the acrylate functionality in curable dental compositions. The ethylenically unsaturated monomer may comprise various ethylenically unsaturated monomers, as known in the art, for use in dental compositions.

In favored embodiments, the (e.g. dental) composition comprises one or more dental resins having a low volume shrinkage monomer. Preferred (e.g. filled) curable dental compositions (useful for restorations such as fillings and crowns) comprise one or more low volume shrinkage resins such that the composition exhibits a Watts Shrinkage of less than about 2%, preferably no greater than 1.80%, more no greater than 1.60%. In favored embodiments, the Watts Shrinkage is no greater than 1.50%, or no greater than 1.40%, or no greater than 1.30%, and in some embodiments no greater than 1.25%, or no greater than 1.20%, or no greater than 1.15%, or no greater than 1.10%.

Preferred low volume shrinkage monomers include isocyanurate resins, such as described in U.S.S.N. 2011/027523 (Abuelyaman et al.); tricyclodecane resins, such as described in U.S.S.N 2011/041736; polymerizable resins having at least one cyclic allylic sulfide moiety such as described in U.S. Pat. No. 7,888,400 (Abuelyaman et al.); methylene dithiepane silane resins as described in U.S. Pat. No. 6,794,520 (Moszner et al.); and di-, tri, and/or tetra-(meth)acryloyl-containing resins such as described in U.S. 2010/021869 (Abuelyaman et al.); each of which are incorporated herein by reference.

In favored embodiments, the majority of the (e.g. unfilled) polymerizable resin composition comprises one or more low volume shrinkage monomers ("Low shrinkage monomers"). For example, at least 50%, 60%, 70%, 80%, 90% or more of the (e.g. unfilled) polymerizable resin may comprise low volume shrinkage monomer(s).

In one embodiment, the dental composition comprises at least one isocyanurate resin. The isocyanurate resin comprises a trivalent isocyanuric acid ring as an isocyanurate core structure and at least two ethylenically unsaturated (e.g. free radically) polymerizable groups bonded to at least two of the nitrogen atoms of the isocyanurate core structure via a (e.g. divalent) linking group. The linking group is the entire chain of atoms between the nitrogen atom of the isocyanurate core structure and the terminal ethylenically unsaturated group. The ethylenically unsaturated (e.g. free radically) polymerizable groups are generally bonded to the core or backbone unit via a (e.g. divalent) linking group.

The trivalent isocyanurate core structure generally has the formula:

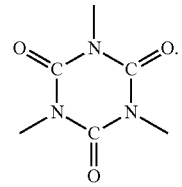

The divalent linking group comprises at least one nitrogen, oxygen or sulfur atom. Such nitrogen, oxygen or sulfur atom forms an urethane, ester, thioester, ether, or thioether linkage. Ether and especially ester linkages can be beneficial over isocyanurate resin comprising urethane linkages for providing improved properties such as reduced shrinkage, and/or increased mechanical properties, e.g., diametral tensile strength (DTS). Thus, in some embodiments, the divalent linking groups of the isocyanurate resin are free of urethane linkages. In some favored embodiments, the divalent linking group comprises an ester linkage such as an aliphatic or aromatic diester linkage.

The isocyanurate monomer typically has the general structure:

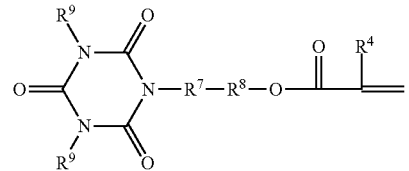

wherein $R^7$ is a (hetero)hydrocarbyl group including straight chain, branched or cyclic alkylene, arylene, or alkarylene, and optionally including a heteroatom (e.g. oxygen, nitrogen, or sulfur); $R^4$ is hydrogen or C1-C4 alkyl; $R^8$ is heterohydrocarbyl group including alkylene, arylene, or alkarylene linking group comprising at least one moiety selected from urethane, ester, thioester, ether, or thioether, and combinations of such moieties; and at least one of the $R^9$ groups is

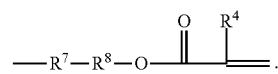

$R^7$ is typically a straight chain, branched or cyclic alkylene, optionally including a heteroatom, having no greater than 12 carbons atoms. In some favored embodiments, $R^7$ has no greater than 8, 6, or 4 carbon atoms. In some favored embodiments, $R_7$ comprises at least one hydroxyl moiety.

In some embodiments, $R^8$ comprises an aliphatic or aromatic ester linkage such as a diester linkage.

In some embodiment, $R^8$ further comprises one or more ether moieties. Hence, the linking group may comprise a combination of ester or diester moieties and one or more ether moieties.

For embodiments, wherein the isocyanurate monomer is a di(meth)acrylate monomer, $R^9$ is hydrogen, alkyl, aryl, or alkaryl, optionally including a heteroatom.

The polymerizable resin portion of the curable unfilled dental composition described herein may comprise at least 10 wt-%, 15 wt-%, 20 wt-%, or 25 wt-%, multifunctional ethylenically unsaturated isocyanurate resin(s). The isocyanurate resin may comprise a single monomer or a blend of two or more isocyanurate resins. The total amount of isocyanurate resin(s) in the unfilled polymerizable resin portion of the curable dental composition is typically no greater than 90 wt-%, 85 wt-%, 80 wt-%, or 75 wt-%.

The filled curable dental composition described herein typically comprises at least 5 wt-%, 6 wt-%, 7 wt-%, 8 wt-%, or 9 wt-% of multifunctional ethylenically unsaturated isocyanurate resin(s). The total amount of isocyanurate resin(s) of the filled hardenable (i.e. polymerizable) dental composition is typically no greater than 20 wt-%, or 19 wt-%, or 18 wt-%, or 17 wt-%, or 16 wt-%, or 15 wt-%.

In another embodiment, the dental composition comprises at least one tricyclodecane resin. The tricyclodecane resin may comprise a single monomer or a blend of two or more tricyclodecane resins. The concentration of multifunctional ethylenically unsaturated tricyclodecane monomer in the (i.e. unfilled) polymerizable resin portion or filled hardenable (i.e. polymerizable) composition can be the same as just described for the multifunctional ethylenically unsaturated isocyanurate monomer.

Tricyclodecane monomers generally have the core structure (i.e. backbone unit (U)):

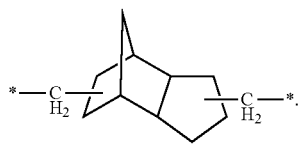

The backbone unit (U) if the tricyclodecane resin typically comprises one or two spacer unit(s) (S) bonded to the backbone unit (U) via an ether linkage. At least one spacer unit (S) comprises a CH(R10)-OG chain, wherein each group G comprises a (meth)acrylate moiety and R10 (comprises at least one group selected from hydrogen, alkyl, aryl, alkaryl and combinations thereof. In some embodiments, R10 is hydrogen, methyl, phenyl, phenoxymethyl, and combinations thereof. G may be bonded to the spacer unit(s) (S) via a urethane moiety.

In some embodiments, the spacer unit(s) (S) typically comprise

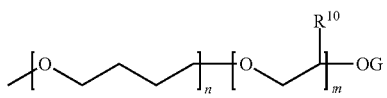

wherein m is 1 to 3; n is 1 to 3; and $R^{10}$ is hydrogen, methyl, phenyl, phenoxymethyl.

In other embodiments, the spacer unit(s) (S) typically comprise

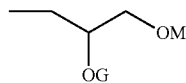

wherein M=aryl.

In some embodiments the composition comprises a multifunctional ethylenically unsaturated isocyanurate monomer and multifunctional ethylenically unsaturated tricyclodecane monomer at a weight ratio ranging from about 1.5:1 to 1:1.5.

In some embodiments, the curable dental composition comprises a polymerizable resin having at least one cyclic allylic sulfide moiety with at least one (meth)acryloyl moiety.

The cyclic allylic sulfide moiety typically comprises at least one 7- or 8-membered ring that has two heteroatoms in the ring, one of which is sulfur. Most typically both of the heteroatoms are sulfur, which may optionally be present as part of an SO, $SO_2$, or S—S moiety. In other embodiments, the ring may comprise a sulfur atom plus a second, different heteroatom in the ring, such as oxygen or nitrogen. In addition, the cyclic allylic moiety may comprise multiple ring structures, i.e. may have two or more cyclic allylic sulfide moieties. The (meth)acryloyl moiety is preferably a (meth) acryloyloxy (i.e. a (meth)acrylate moiety) or a (meth)acryloylamino (i.e., a (meth)acrylamide moiety).

In one embodiment, the low shrinkage resin includes those represented by the formulae:

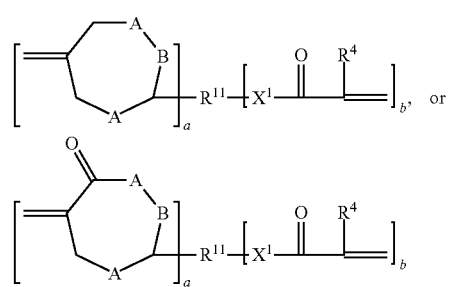

In the above formulae, each A can be independently selected from S, O, N, C (e.g., $C(R^{10})_2$, where each $R^{10}$ is independently a H or an organic group), SO, $SO_2$, N-alkyl, N-acyl, NH, N-aryl, carboxyl or carbonyl group, provided that at least one X is S or a group comprising S. Preferably, each A is sulfur.

B is either alkylene (e.g., methylene, ethylene, etc.) optionally including a heteroatom, carbonyl, or acyl; or is absent, thereby indicating the size of the ring, typically 7- to 10-membered rings, however larger rings are also contemplated. Preferably, the ring is either a 7- or 8-membered ring with Y thus being either absent or methylene, respectively. In some embodiments, Y is either absent or is a C1 to C3 alkylene, optionally including a heteroatom, carbonyl, acyl, or combinations thereof.

$X^1$ is independently —O— or —$NR^4$—, where $R^4$ is H or $C_1$-$C_4$ alkyl.

The $R^{11}$ group represents a linker selected from alkylene (typically having more than one carbon atom, i.e. excluding methylene), alkylene optionally including a heteroatom (e.g., O, N, S, S—S, SO, SO2), arylene, cycloaliphatic, carbonyl, siloxane, amido (—CO—NH—), acyl (—CO—O—), urethane (—O—CO—NH—), and urea (—NH—CO—NH—) groups, and combinations thereof. In certain embodiments, R' comprises an alkylene group, typically a methylene or longer group, that may be either straight chain or branched, and which can be either unsubstituted, or substituted with aryl, cycloalkyl, halogen, nitrile, alkoxy, alkylamino, dialkylamino, akylthio, carbonyl, acyl, acyloxy, amido, urethane group, urea group, a cyclic allylic sulfide moiety, or combinations thereof.

$R^4$ is H or $C_1$-$C_4$ alkyl, and "a" and "b" are independently 1 to 3.

Optionally the cyclic allylic sulfide moiety can further be substituted on the ring with one or more groups selected from straight or branched chain alkyl, aryl, cycloalkyl, halogen, nitrile, alkoxy, alkylamino, dialkylamino, akylthio, carbonyl, acyl, acyloxy, amido, urethane group, and urea group. Preferably the selected substituents do not interfere with the hardening reaction. Preferred are cyclic allylic sulfide structures that comprise unsubstituted methylene members.

A typical low shrinkage monomer can comprise an 8-membered cyclic allylic sulfide moiety with two sulfur atoms in the ring and with the linker attached directly to the 3-position of the ring with an acyl group (i.e., Ring-OC(O)—). Typically the weight average molecular weight (MW) of the hybrid monomer ranges from about 400 to about 900 and in some embodiments is at least 250, more typically at least 500, and most typically at least 800.

The inclusion of a polymerizable compound having at least one cyclic allylic sulfide moiety can result in a synergistic combination of low volume shrinkage in combination with high diametral tensile strength.

In another embodiment, the dental composition comprises a low shrinkage resin that includes at least one di-, tri-, and/or tetra(meth)acryloyl-containing resins having the general formula:

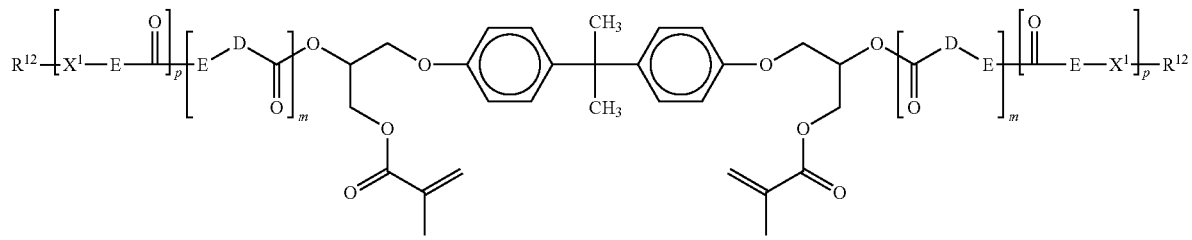

wherein:
each $X^1$ is independently —O— or —$NR^4$—, where $R^4$ is H or $C_1$-$C_4$ alkyl;
D and E each independently represent an organic group, and $R^{12}$ represents —C(O)C($CH_3$)=$CH_2$, and/or (ii) q=0 and $R^2$ represents —H, —C(O)CH=$CH_2$,
or —C(O)C($CH_3$)=$CH_2$, with the proviso that at least one $R^{12}$ is a (meth)acrylate; each m is 1 to 5; p and q are independently 0 or 1. Although this material is a derivative of bisphenol A, when other low volume shrinkage monomer are employed, such as the isocyanurate and/or tricyclodecane monomer, the dental composition is free of (meth)acrylate monomers derived from bisphenol A.

In another embodiment, the low shrinkage dental resin may be selected from methylene dithiepane silane resins described in U.S. Pat. No. 6,794,520 (Moszner et al.), incorporated herein by reference. Such resins have the general formula

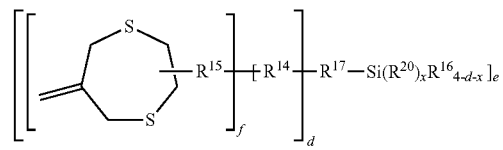

in which $R^{14}$ is a saturated or unsaturated aliphatic or alicyclic hydrocarbon radical with 1 to 10 carbon atoms, which can be interrupted by one or more oxygen and/or sulfur atoms and can contain one or more ester, carbonyl, amide and/or urethane groups, or is an aromatic or heteroaromatic hydrocarbon radical with 6 to 18 carbon atoms, the hydrocarbon radicals being able to be substituted or unsubstituted; $R^{15}$ has one of the meanings given for $R^{14}$ or is absent; $R^{16}$ has one of the meanings given for $R^{14}$ or is absent; $R^{17}$ is equal to —(CHR$^{19}$)$_n$—, —W—CO—NH—(CHR$^{19}$)$_n$—, —Y—CO—NH—$R^{18}$—, —(CHR$^{19}$)$_n$—, —SR$^{18}$—, —CO—O—$R^{18}$— or is absent, with n being equal to 1 to 4, $R^{19}$ is hydrogen, $C_1$ to $C_{10}$ alkyl or $C_6$ to $C_{10}$ aryl, $R^{18}$ has one of the meanings given for $R^{14}$ and W stands for an O or S atom or is absent; with $R^{18}$ and $R^{19}$ being able to be substituted or unsubstituted; $R^{20}$ is a hydrolyzable group; d, e, f and x each independently of each other being 1, 2 or 3; and the sum of d+x=2 to 4.

The multifunctional low shrink resins are (e.g. highly) viscous liquids at about 25° C., yet are flowable. The viscosity as can be measured with a Haake RotoVisco RV1 device, as described in EP Application No. 10168240.9, filed Jul. 2, 2010 is typically at least 300, or 400, or 500 Pa*s and no greater than 10,000 Pascal-seconds (Pa*s). In some embodiments, the viscosity is no greater than 5000 or 2500 Pa*s.

The ethylenically unsaturated resins of the dental composition are typically stable liquids at about 25° C. meaning that the resins do not substantially polymerize, crystallize, or otherwise solidify when stored at room temperature (about 25° C.) for a typical shelf life of at least 30, 60, or 90 days. The viscosity of the resins typically does not change (e.g. increase) by more than 10% of the initial viscosity.

Particularly for dental restoration compositions, the ethylenically unsaturated resins generally have a refractive index of at least 1.50. In some embodiments, the refractive index is at least 1.51, 1.52, 1.53, or greater. The inclusion of sulfur atoms and/or the present of one or more aromatic moieties can raise the refractive index (relative to the same molecular weight resin lacking such substituents).

In some embodiments, the (unfilled) polymerizable resin may comprise solely one or more low shrink resins in combination with the addition fragmentation agent(s). In other embodiments, the (unfilled) polymerizable resin comprises a small concentration of other monomer(s). By "other" is it meant an ethylenically unsaturated monomer such as a (meth)acrylate monomer that is not a low volume shrinkage monomer.

The concentration of such other monomer(s) is typically no greater than 20 wt-%, 19 wt-%, 18 wt-%, 17 wt-%, 16 wt-%, or 15 wt-% of the (unfilled) polymerizable resin portion. The concentration of such other monomers is typically no greater than 5 wt-%, 4 wt-%, 3 wt-%, or 2 wt-% of the filled polymerizable dental composition.

In some embodiments, the "other monomers" of the dental composition comprise a low viscosity reactive (i.e. polymerizable) diluent. Reactive diluents typically have a viscosity as can be measured with a Haake RotoVisco RV1 device, as described in EP Application No. 10168240.9, filed Jul. 2, 2010 of no greater than 300 Pa*s and preferably no greater than 100 Pa*s, or 50 Pa*s, or 10 Pa*s. In some embodiments, the reactive diluent has a viscosity no greater than 1 or 0.5 Pa*s. Reactive diluents are typically relatively low in molecular weight, having a molecular weight less than 600 g/mole, or 550 g/mol, or 500 g/mole. Reactive diluents typically comprise one or two ethylenically unsaturated groups such as in the case of mono(meth)acrylate or di(meth)acrylate monomers.

In some embodiments, the reactive diluent is an isocyanurate or tricyclodecane monomer. Tricyclodecane reactive diluent may have the same generally structure as previously described. In favored embodiments, the tricyclodecane reactive diluent comprises one or two spacer unit(s) (S) being connected to the backbone unit (U) via an ether linkage; such as described in U.S. 2011/041736 (Eckert et al.); incorporated herein by reference.

Although the inclusion of an addition fragmentation agent in a low volume shrinkage composition typically provides the lowest stress and/or lowest shrinkage, the addition fragmentation agents described herein can also reduce the stress of dental composition comprising conventional hardenable (meth)acrylate monomers, such as ethoxylated bisphenol A dimethacrylate (BisEMA6), 2-hydroxyethyl methacrylate (HEMA), bisphenol A diglycidyl dimethacrylate (bisGMA), urethane dimethacrylate (UDMA), triethlyene glycol dimethacrylate (TEGDMA), glycerol dimethacrylate (GDMA), ethylenegylcol dimethacrylate, neopentylglycol dimethacrylate (NPGDMA), and polyethyleneglycol dimethacrylate (PEGDMA).

The curable component of the curable dental composition can include a wide variety of "other" ethylenically unsaturated compounds (with or without acid functionality), epoxy-functional (meth)acrylate resins, vinyl ethers, and the like.

The (e.g., photopolymerizable) dental compositions may include free radically polymerizable monomers, oligomers, and polymers having one or more ethylenically unsaturated groups. Suitable compounds contain at least one ethylenically unsaturated bond and are capable of undergoing addition polymerization. Examples of useful ethylenically unsaturated compounds include acrylic acid esters, methacrylic acid esters, hydroxy-functional acrylic acid esters, hydroxy-functional methacrylic acid esters, and combinations thereof.

Such free radically polymerizable compounds include mono-, di- or poly-(meth)acrylates (i.e., acrylates and methacrylates) such as, methyl (meth)acrylate, ethyl (meth)acrylate, isopropyl (meth)acrylate, n-hexyl (meth)acrylate, stearyl (meth)acrylate, allyl (meth)acrylate, glycerol tri (meth)acrylate, ethyleneglycol di(meth)acrylate, diethyleneglycol di(meth)acrylate, triethyleneglycol di(meth)acrylate, 1,3-propanediol di(meth)acrylate, trimethylolpropane tri(meth)acrylate, 1,2,4-butanetriol tri(meth)acrylate, 1,4-cyclohexanediol di(meth)acrylate, pentaerythritol tetra(meth)acrylate, sorbitol hex(meth)acrylate, tetrahydrofurfuryl (meth)acrylate, bis[1-(2-acryloxy)]-p-ethoxyphenyldimethylmethane, bis[1-(3-acryloxy-2-hydroxy)]-p-propoxyphenyldimethylmethane, ethoxylated bisphenol A di(meth)acrylate, and trishydroxyethyl-isocyanurate tri(meth)acrylate; (meth)acrylamides (i.e., acrylamides and methacrylamides) such as (meth)acrylamide, methylene bis-(meth)acrylamide, and diacetone (meth)acrylamide; urethane (meth)acrylates; the bis-(meth)acrylates of polyethylene glycols (preferably of molecular weight 200-500); and vinyl compounds such as styrene, diallyl phthalate, divinyl succinate, divinyl adipate and divinyl phthalate. Other suitable free radically polymerizable compounds include siloxane-functional (meth)acrylates. Mixtures of two or more free radically polymerizable compounds can be used if desired.

The curable dental composition may also contain a monomer having hydroxyl groups and ethylenically unsaturated groups as an example of an "other monomer". Examples of such materials include hydroxyalkyl (meth)acrylates, such as 2-hydroxyethyl (meth)acrylate and 2-hydroxypropyl (meth) acrylate; glycerol mono- or di-(meth)acrylate; trimethylolpropane mono- or di-(meth)acrylate; pentaerythritol mono-, di-, and tri-(meth)acrylate; sorbitol mono-, di-, tri-, tetra-, or penta-(meth)acrylate; and 2,2-bis[4-(2-hydroxy-3-methacryloxypropoxy)phenyl]propane (bisGMA). Suitable ethylenically unsaturated compounds are available from a wide variety of commercial sources, such as Sigma-Aldrich, St. Louis.

The curable dental compositions can include at least 1 wt-%, at least 3 wt-%, or at least 5 wt-% ethylenically unsaturated compounds with hydroxyl functionality, based on the total weight of the unfilled composition. The compositions can include at most 80 wt-%, at most 70 wt-%, or at most 60 wt-% ethylenically unsaturated compounds with hydroxyl functionality.

The dental compositions described herein may include one or more curable components in the form of ethylenically unsaturated compounds with acid functionality as an example of an "other" monomer. When present, the polymerizable component optionally comprises an ethylenically unsaturated compound with acid functionality. Preferably, the acid functionality includes an oxyacid (i.e., an oxygen-containing acid) of carbon, sulfur, phosphorous, or boron. Such acid-functional "other" monomers contribute to the self-adhesion or self-etching of the dental compositions as described in U.S. 2005/017966 (Falsafi et al.), incorporated herein by reference.

As used herein, ethylenically unsaturated compounds with acid functionality is meant to include monomers, oligomers, and polymers having ethylenic unsaturation and acid and/or acid-precursor functionality. Acid-precursor functionalities include, for example, anhydrides, acid halides, and pyrophosphates. The acid functionality can include carboxylic acid functionality, phosphoric acid functionality, phosphonic acid functionality, sulfonic acid functionality, or combinations thereof.

Ethylenically unsaturated compounds with acid functionality include, for example, α,β-unsaturated acidic compounds such as glycerol phosphate mono(meth)acrylates, glycerol phosphate di(meth)acrylates, hydroxyethyl (meth) acrylate (e.g., HEMA) phosphates, bis((meth)acryloxyethyl) phosphate, ((meth)acryloxypropyl)phosphate, bis((meth) acryloxypropyl)phosphate, bis((meth)acryloxy)propyloxy phosphate, (meth)acryloxyhexyl phosphate, bis((meth)acryloxyhexyl)phosphate, (meth)acryloxyoctyl phosphate, bis ((meth)acryloxyoctyl)phosphate, (meth)acryloxydecyl phosphate, bis((meth)acryloxydecyl)phosphate, caprolactone methacrylate phosphate, citric acid di- or tri-methacrylates, poly(meth)acrylated oligomaleic acid, poly(meth)acrylated polymaleic acid, poly(meth)acrylated poly(meth)acrylic acid, poly(meth)acrylated polycarboxyl-polyphosphonic acid, poly(meth)acrylated polychlorophosphoric acid, poly (meth)acrylated polysulfonate, poly(meth)acrylated polyboric acid, and the like, may be used as components. Also monomers, oligomers, and polymers of unsaturated carbonic acids such as (meth)acrylic acids, aromatic (meth)acrylated acids (e.g., methacrylated trimellitic acids), and anhydrides thereof can be used.

The dental compositions can include an ethylenically unsaturated compound with acid functionality having at least one P—OH moiety. Such compositions are self-adhesive and are non-aqueous. For example, such compositions can include: a first compound including at least one (meth)acryloxy group and at least one —O—P(O)(OH)$_x$ group, wherein x=1 or 2, and wherein the at least one —O—P(O)(OH)$_x$ group and the at least one (meth)acryloxy group are linked together by a $C_1$-$C_4$ hydrocarbon group; a second compound including at least one (meth)acryloxy group and at least one —O—P(O)(OH)$_x$ group, wherein x=1 or 2, and wherein the at least one —O—P(O)(OH)$_x$ group and the at least one (meth)acryloxy group are linked together by a $C_5$-$C_{12}$ hydrocarbon group; an ethylenically unsaturated compound without acid functionality; an initiator system; and a filler.

The curable dental compositions can include at least 1 wt-%, at least 3 wt-%, or at least 5 wt-% ethylenically unsaturated compounds with acid functionality, based on the total weight of the unfilled composition. The compositions can include at most 80 wt-%, at most 70 wt-%, or at most 60 wt-% ethylenically unsaturated compounds with acid functionality.

The curable dental compositions may include resin-modified glass ionomer cements such as those described in U.S. Pat. No. 5,130,347 (Mitra), U.S. Pat. No. 5,154,762 (Mitra), U.S. Pat. No. 5,925,715 (Mitra et al.) and U.S. Pat. No. 5,962,550 (Akahane). Such compositions can be powder-liquid, paste-liquid or paste-paste systems. Alternatively, copolymer formulations such as those described in U.S. Pat. No. 6,126,922 (Rozzi) are included in the scope of the invention.

An initiator is typically added to the mixture of polymerizable ingredients (i.e. curable resins and AFM). The initiator is sufficiently miscible with the resin system to permit ready dissolution in (and discourage separation from) the polymerizable composition. Typically, the initiator is present in the composition in effective amounts, such as from about 0.1 weight percent to about 5.0 weight percent, based on the total weight of the composition.

The addition-fragmentation agent is generally free-radically cleavable. Although photopolymerization is one mechanism for generating free radicals, other curing mechanisms also generate free radicals. Thus, the addition-fragmentation agent does not require irradiation with actinic radiation (e.g. photocuring) in order to provide the reduction in stress during curing.

In some embodiments, the mixture of resins is photopolymerizable and the composition contains a photoinitiator (i.e., a photoinitiator system) that upon irradiation with actinic radiation initiates the polymerization (or hardening) of the composition. Such photopolymerizable compositions can be free radically polymerizable. The photoinitiator typically has a functional wavelength range from about 250 nm to about 800 nm.

Suitable photoinitiators (i.e., photoinitiator systems that include one or more compounds) for polymerizing free radically photopolymerizable compositions include binary and tertiary systems. Typical tertiary photoinitiators include an iodonium salt, a photosensitizer, and an electron donor compound as described in U.S. Pat. No. 5,545,676 (Palazzotto et al.). Iodonium salts include diaryl iodonium salts, e.g., diphenyliodonium chloride, diphenyliodonium hexafluorophosphate, and diphenyliodonium tetrafluoroboarate. Some preferred photosensitizers may include monoketones and diketones (e.g. alpha diketones) that absorb some light within a range of about 300 nm to about 800 nm (preferably, about 400 nm to about 500 nm) such as camphorquinone, benzil, furil, 3,3,6,6-tetramethylcyclohexanedione, phenanthraquinone and other cyclic alpha diketones. Of these camphorquinone is typically preferred. Preferred electron donor compounds include substituted amines, e.g., ethyl 4-(N,N-dimethylamino)benzoate.

Other suitable photoinitiators for polymerizing free radically photopolymerizable compositions include the class of phosphine oxides that typically have a functional wavelength range of about 380 nm to about 1200 nm. Preferred phosphine oxide free radical initiators with a functional wavelength range of about 380 nm to about 450 nm are acyl and bisacyl phosphine oxides.

Commercially available phosphine oxide photoinitiators capable of free-radical initiation when irradiated at wavelength ranges of greater than about 380 nm to about 450 nm include bis(2,4,6-trimethylbenzoyl)phenyl phosphine oxide (IRGACURE 819, Ciba Specialty Chemicals, Tarrytown, N.Y.), bis(2,6-dimethoxybenzoyl)-(2,4,4-trimethylpentyl) phosphine oxide (CGI 403, Ciba Specialty Chemicals), a 25:75 mixture, by weight, of bis(2,6-dimethoxybenzoyl)-2, 4,4-trimethylpentyl phosphine oxide and 2-hydroxy-2-methyl-1-phenylpropan-1-one (IRGACURE 1700, Ciba Specialty Chemicals), a 1:1 mixture, by weight, of bis(2,4,6-trimethylbenzoyl)phenyl phosphine oxide and 2-hydroxy-2-methyl-1-phenylpropane-1-one (DAROCUR 4265, Ciba Specialty Chemicals), and ethyl 2,4,6-trimethylbenzylphenyl phosphinate (LUCIRIN LR8893X, BASF Corp., Charlotte, N.C.).

Tertiary amine reducing agents may be used in combination with an acylphosphine oxide. Illustrative tertiary amines include ethyl 4-(N,N-dimethylamino)benzoate and N,N-dimethylaminoethyl methacrylate. When present, the amine reducing agent is present in the photopolymerizable composition in an amount from about 0.1 weight percent to about 5.0 weight percent, based on the total weight of the composition. In some embodiments, the curable dental composition may be irradiated with ultraviolet (UV) rays. For this embodiment, suitable photoinitiators include those available under the trade designations IRGACURE and DAROCUR from Ciba Speciality Chemical Corp., Tarrytown, N.Y. and include 1-hydroxy cyclohexyl phenyl ketone (IRGACURE 184), 2,2-dimethoxy-1,2-diphenylethan-1-one (IRGACURE 651), bis (2,4,6-trimethylbenzoyl)phenylphosphineoxide (IRGACURE 819), 1-[4-(2-hydroxyethoxy)phenyl]-2-hydroxy-2-methyl-1-propane-1-one (IRGACURE 2959), 2-benzyl-2-dimethylamino-1-(4-morpholinophenyl)butanone (IRGACURE 369), 2-methyl-1-[4-(methylthio)phenyl]-2-morpholinopropan-1-one (IRGACURE 907), and 2-hydroxy-2-methyl-1-phenyl propan-1-one (DAROCUR 1173).

The photoinitiator may also be a polymerizable photoinitiator having a free-radically polymerizable groups and a photoinitiator group. Such polymerizable photoinitiators include 4-benzoylphenyl acrylate, 2-(4-benzoylphenoxy) ethyl acrylate and 2-[4-(2-hydroxy-2-methylpropanoyl)phenoxy]ethyl-N-acryloyl-2-methylalinate, and are described in U.S. Pat. No. 7,838,110 (Zhu et al.), U.S. Pat. No. 5,506,279 (Babu et al.), incorporated herein by reference, and also Temel et al. "Photopolymerization and photophysical properties of amine linked benzophenone photoinitiators for free radical polymerization", Journal of Photochemistry and Photobiology A, Chemistry 219 (2011), pp. 26-31.

The initiator is used in an amount effective to facilitate free radical addition to the addition-fragmentation crosslinking agent and the amount will vary depending upon, e.g., the type of initiator and the molecular weight of the polymer and the degree of functionalization desired. The initiators can be used in amounts from about 0.001 part by weight to about 5 parts by weight based on 100 parts total monomer.

The photopolymerizable compositions are typically prepared by admixing the various components of the compositions. For embodiments wherein the photopolymerizable compositions are not cured in the presence of air, the photoinitiator is combined under "safe light" conditions (i.e., conditions that do not cause premature hardening of the composition). Suitable inert solvents may be employed if desired when preparing the mixture.

Curing is affected by exposing the composition to a radiation source, preferably a visible light source. It is convenient to employ light sources that emit actinic radiation light between 250 nm and 800 nm (particularly blue light of a wavelength of 380-520 nm) such as quartz halogen lamps, tungsten-halogen lamps, mercury arcs, carbon arcs, low-, medium-, and high-pressure mercury lamps, plasma arcs, light emitting diodes, and lasers. In general, useful light sources have intensities in the range of 0.200-1000 W/cm$^2$. A variety of conventional lights for hardening such compositions can be used.

The exposure may be accomplished in several ways. For example, the polymerizable composition may be continuously exposed to radiation throughout the entire hardening process (e.g., about 2 seconds to about 60 seconds). It is also possible to expose the composition to a single dose of radiation, and then remove the radiation source, thereby allowing polymerization to occur. In some cases materials can be subjected to light sources that ramp from low intensity to high intensity. Where dual exposures are employed, the intensity of each dosage may be the same or different. Similarly, the total energy of each exposure may be the same or different.

The dental compositions comprising the multifunctional ethylenically unsaturated monomers may be chemically curable, i.e., the compositions contain a chemical initiator (i.e., initiator system) that can polymerize, cure, or otherwise harden the composition without dependence on irradiation with actinic radiation. Such chemically curable (e.g., polymerizable or curable) composition are sometimes referred to as "self-cure" compositions and may include redox cure systems, thermally curing systems and combinations thereof. Further, the polymerizable composition may comprise a combination of different initiators, at least one of which is suitable for initiating free radical polymerization.

The chemically hardenable compositions may include redox cure systems that include a polymerizable component (e.g., an ethylenically unsaturated polymerizable component) and redox agents that include an oxidizing agent and a reducing agent.

The reducing and oxidizing agents react with or otherwise cooperate with one another to produce free-radicals capable of initiating polymerization of the resin system (e.g., the ethylenically unsaturated component). This type of cure is a dark reaction, that is, it is not dependent on the presence of light and can proceed in the absence of light. The reducing and oxidizing agents are preferably sufficiently shelf-stable and free of undesirable colorization to permit their storage and use under typical conditions.

Useful reducing agents include ascorbic acid, ascorbic acid derivatives, and metal complexed ascorbic acid compounds as described in U.S. Pat. No. 5,501,727 (Wang et al.); amines, especially tertiary amines, such as 4-tert-butyl dimethylaniline; aromatic sulfinic salts, such as p-toluenesulfinic salts and benzenesulfinic salts; thioureas, such as 1-ethyl-2-thiourea, tetraethyl thiourea, tetramethyl thiourea, 1,1-dibutyl thiourea, and 1,3-dibutyl thiourea; and mixtures thereof. Other secondary reducing agents may include cobalt (II) chloride, ferrous chloride, ferrous sulfate, hydrazine, hydroxylamine (depending on the choice of oxidizing agent), salts of a dithionite or sulfite anion, and mixtures thereof. Preferably, the reducing agent is an amine.

Suitable oxidizing agents will also be familiar to those skilled in the art, and include but are not limited to persulfuric acid and salts thereof, such as sodium, potassium, ammonium, cesium, and alkyl ammonium salts. Additional oxidizing agents include peroxides such as benzoyl peroxides, hydroperoxides such as cumyl hydroperoxide, t-butyl hydroperoxide, and amyl hydroperoxide, as well as salts of transition metals such as cobalt (III) chloride and ferric chloride, cerium (IV) sulfate, perboric acid and salts thereof, permanganic acid and salts thereof, perphosphoric acid and salts thereof, and mixtures thereof.

It may be desirable to use more than one oxidizing agent or more than one reducing agent. Small quantities of transition metal compounds may also be added to accelerate the rate of redox cure. The reducing or oxidizing agents can be microencapsulated as described in U.S. Pat. No. 5,154,762 (Mitra et al.). This will generally enhance shelf stability of the polymerizable composition, and if necessary permit packaging the reducing and oxidizing agents together. For example, through appropriate selection of an encapsulant, the oxidizing and reducing agents can be combined with an acid-functional component and optional filler and kept in a storage-stable state.

Curable dental compositions can also be cured with a thermally or heat activated free radical initiator. Typical thermal initiators include peroxides such as benzoyl peroxide and azo compounds such as azobisisobutyronitrile, as well as dicumyl peroxide, which is favored for mill blanks In favored embodiments, such as when the dental composition is employed as a dental restorative (e.g. dental filling or crown) or an orthodontic cement, the dental composition typically comprises appreciable amounts of (e.g. nanoparticle) filler. The amount of such fillers is a function of the end use as further described herein. Such compositions preferably include at least 40 wt-%, more preferably at least 45 wt-%, and most preferably at least 50 wt-% filler, based on the total weight of the composition. In some embodiments the total amount of filler is at most 90 wt-%, preferably at most 80 wt-%, and more preferably at most 75 wt-% filler.

The (e.g. filled) dental composite materials typically exhibit a diametral tensile strength (DTS) of at least about 70, 75, or 80 MPa and/or a Barcol Hardness of at least about 60, or 65, or 70. The depth of cure ranges from about 4 to about 5 and comparable to commercially available (e.g. filled) dental compositions suitable for restorations.

Dental compositions suitable for use as dental adhesives can optionally also include filler in an amount of at least 1 wt-%, 2 wt-%, 3 wt-%, 4 wt-%, or 5 wt-% based on the total weight of the composition. For such embodiments, the total concentration of filler is at most 40 wt-%, preferably at most 20 wt-%, and more preferably at most 15 wt-% filler, based on the total weight of the composition.

Fillers may be selected from one or more of a wide variety of materials suitable for incorporation in compositions used for dental applications, such as fillers currently used in dental restorative compositions, and the like.

The filler can be an inorganic material. It can also be a crosslinked organic material that is insoluble in the polymerizable resin, and is optionally filled with inorganic filler. The filler is generally non-toxic and suitable for use in the mouth. The filler can be radiopaque, radiolucent, or nonradiopaque. Fillers as used in dental applications are typically ceramic in nature.

Suitable inorganic filler particles include quartz (i.e., silica), submicron silica, zirconia, submicron zirconia, and non-vitreous microparticles of the type described in U.S. Pat. No. 4,503,169 (Randklev).

The filler can also be an acid-reactive filler. Suitable acid-reactive fillers include metal oxides, glasses, and metal salts. Typical metal oxides include barium oxide, calcium oxide, magnesium oxide, and zinc oxide. Typical glasses include borate glasses, phosphate glasses, and fluoroaluminosilicate ("FAS") glasses. The FAS glass typically contains sufficient elutable cations so that a hardened dental composition will form when the glass is mixed with the components of the hardenable composition. The glass also typically contains sufficient elutable fluoride ions so that the hardened composition will have cariostatic properties. The glass can be made from a melt containing fluoride, alumina, and other glass-forming ingredients using techniques familiar to those skilled in the FAS glassmaking art. The FAS glass typically is in the form of particles that are sufficiently finely divided so that they can conveniently be mixed with the other cement components and will perform well when the resulting mixture is used in the mouth.

Generally, the average particle size (typically, diameter) for the FAS glass is no greater than 12 micrometers, typically no greater than 10 micrometers, and more typically no greater than 5 micrometers as measured using, for example, a sedimentation particle size analyzer. Suitable FAS glasses will be familiar to those skilled in the art, and are available from a wide variety of commercial sources, and many are found in currently available glass ionomer cements such as those commercially available under the trade designations VITREMER, VITREBOND, RELY X LUTING CEMENT, RELY X LUTING PLUS CEMENT, PHOTAC-FIL QUICK, KETAC-MOLAR, and KETAC-FIL PLUS (3M ESPE Dental Products, St. Paul, Minn.), FUJI II LC and FUJI IX (G-C Dental Industrial Corp., Tokyo, Japan) and CHEMFIL Superior (Dentsply International, York, Pa.). Mixtures of fillers can be used if desired.

Other suitable fillers are disclosed in U.S. Pat. No. 6,387,981 (Zhang et al.) and U.S. Pat. No. 6,572,693 (Wu et al.) as well as PCT International Publication Nos. WO 01/30305 (Zhang et al.), U.S. Pat. No. 6,730,156 (Windisch et al.), WO 01/30307 (Zhang et al.), and WO 03/063804 (Wu et al.). Filler components described in these references include nanosized silica particles, nanosized metal oxide particles, and combinations thereof. Nanofillers are also described in U.S. Pat. No. 7,090,721 (Craig et al.), U.S. Pat. No. 7,090,722 (Budd et al.) and U.S. Pat. No. 7,156,911; and U.S. Pat. No. 7,649,029 (Kolb et al.).

Examples of suitable organic filler particles include filled or unfilled pulverized polycarbonates, polyepoxides, poly(meth)acrylates and the like. Commonly employed dental filler particles are quartz, submicron silica, and non-vitreous microparticles of the type described in U.S. Pat. No. 4,503,169 (Randklev).

Mixtures of these fillers can also be used, as well as combination fillers made from organic and inorganic materials.

Fillers may be either particulate or fibrous in nature. Particulate fillers may generally be defined as having a length to width ratio, or aspect ratio, of 20:1 or less, and more commonly 10:1 or less. Fibers can be defined as having aspect ratios greater than 20:1, or more commonly greater than 100:1. The shape of the particles can vary, ranging from spherical to ellipsoidal, or more planar such as flakes or discs. The macroscopic properties can be highly dependent on the shape of the filler particles, in particular the uniformity of the shape.

Micron-size particles are very effective for improving post-cure wear properties. In contrast, nanoscopic fillers are commonly used as viscosity and thixotropy modifiers. Due to their small size, high surface area, and associated hydrogen bonding, these materials are known to assemble into aggregated networks.

In some embodiments, the dental composition preferably comprise a nanoscopic particulate filler (i.e., a filler that comprises nanoparticles) having an average primary particle size of less than about 0.100 micrometers (i.e., microns), and more preferably less than 0.075 microns. As used herein, the term "primary particle size" refers to the size of a non-associated single particle. The average primary particle size can be determined by cutting a thin sample of hardened dental composition and measuring the particle diameter of about 50-100 particles using a transmission electron micrograph at a magnification of 300,000 and calculating the average. The filler can have a unimodal or polymodal (e.g., bimodal) particle size distribution. The nanoscopic particulate material typically has an average primary particle size of at least about 2 nanometers (nm), and preferably at least about 7 nm. Preferably, the nanoscopic particulate material has an average primary particle size of no greater than about 50 nm, and more preferably no greater than about 20 nm in size. The average surface area of such a filler is preferably at least about 20 square meters per gram ($m^2/g$), more preferably, at least about 50 $m^2/g$, and most preferably, at least about 100 $m^2/g$.

In some preferred embodiments, the dental composition comprises silica nanoparticles. Suitable nano-sized silicas are commercially available from Nalco Chemical Co. (Naperville, Ill.) under the product designation NALCO COLLOIDAL SILICAS. For example, preferred silica particles can be obtained from using NALCO products 1040, 1041, 1042, 1050, 1060, 2327 and 2329.

Silica particles are preferably made from an aqueous colloidal dispersion of silica (i.e., a sol or aquasol). The colloidal silica is typically in the concentration of about 1 to 50 weight percent in the silica sol. Colloidal silica sols that can be used are available commercially having different colloid sizes, see Surface & Colloid Science, Vol. 6, ed. Matijevic, E., Wiley Interscience, 1973. Preferred silica sols for use making the fillers are supplied as a dispersion of amorphous silica in an aqueous medium (such as the Nalco colloidal silicas made by Nalco Chemical Company) and those which are low in sodium concentration and can be acidified by admixture with a suitable acid (e.g. Ludox colloidal silica made by E. I. Dupont de Nemours & Co. or Nalco 2326 from Nalco Chemical Co.).

Preferably, the silica particles in the sol have an average particle diameter of about 5-100 nm, more preferably 10-50 nm, and most preferably 12-40 nm. A particularly preferred silica sol is NALCO™ 1042 or 2327.

In some embodiments, the dental composition comprises zirconia nanoparticles. Suitable nano-sized zirconia nanoparticles can be prepared using hydrothermal technology as described in U.S. Pat. No. 7,241,437 (Davidson et al.).

In some embodiments, lower refractive index (e.g. silica) nanoparticles are employed in combination with high refractive index (e.g. zirconia) nanoparticles in order to index match (refractive index within 0.02) the filler to the refractive index of the polymerizable resin.

In some embodiments, the nanoparticles are in the form of nanoclusters, i.e. a group of two or more particles associated by relatively weak intermolecular forces that cause the particles to clump together, even when dispersed in a hardenable resin. Preferred nanoclusters can comprise a substantially amorphous cluster of non-heavy (e.g. silica) particles, and amorphous heavy metal oxide (i.e. having an atomic number greater than 28) particles such as zirconia. The primary particles of the nanocluster preferably have an average diameter of less than about 100 nm. Suitable nanocluster fillers are described in U.S. Pat. No. 6,730,156 (Windisch et al.); incorporated herein by reference.

In some preferred embodiments, the dental composition comprises nanoparticles and/or nanoclusters surface treated with an organometallic coupling agent to enhance the bond between the filler and the resin. The organometallic coupling agent may be functionalized with reactive curing groups, such as acrylates, methacrylates, vinyl groups and the like and may comprise silane, zirconate or titanate coupling agents. Preferred coupling agents include gamma-methacryloxypropyltrimethoxysilane, gamma-mercaptopropyltriethoxysilane, gamma-aminopropyltrimethoxysilane, and the like.

Suitable copolymerizable or reactive organometallic compounds may have the general formulas: $CH_2=C(R^{22})-R^{21}Si(OR)_nR_{3-n}$ or $CH_2=C(R^{22})-C=OOR^{21}Si(OR)_nR_{3-n}$; wherein R is an $C_1-C_4$ alkyl, $R^{21}$ is a divalent organic heterohydrocarbyl linking group, preferably alkylene; $R^{22}$ is H or C1-C4 alkyl; and n is from 1 to 3. Preferred coupling agents include gamma-methacryloxypropyltrimethoxysilane, gamma-mercaptopropyltriethoxysilane, gamma-aminopropyltrimethoxysilane, and the like.

A variety of methods are available for modifying the surface of nanoparticles including, e.g., adding a surface-modifying agent to nanoparticles (e.g., in the form of a powder or a colloidal dispersion) and allowing the surface-modifying agent to react with the nanoparticles. Other useful surface-modification processes are described in, e.g., U.S. Pat. No. 2,801,185 (Iler), U.S. Pat. No. 4,522,958 (Das et al.) U.S. Pat. No. 6,586,483 (Kolb et al.), each incorporated herein by reference.

Surface-modifying groups may be derived from surface-modifying agents. Schematically, surface-modifying agents can be represented by the formula A-B, where the A group is capable of attaching to the surface of the particle (i.e., the silanol groups of a silica particle) and the B group is a reactive or non-reactive functional group. A non-functional group is one does not react with other components in the system (e.g. the substrate). Non-reactive functional groups can be selected to render the particle relatively more polar, relatively less polar or relatively non-polar. In some embodiments the non-reactive functional group "B" is a hydrophilic group such as au acid group (including carboxylate, sulfonate and phosphonate groups), ammonium group or poly(oxyethylene) group, or hydroxyl group. In other embodiments, "B" may be a reactive functional groups such as an ethylenically unsaturated polymerizable group, including vinyl, allyl, vinyloxy, allyloxy, and (meth)acryloyl, that may be free-radically polymerized with the polymerizable resin or monomers.

Such optional surface-modifying agents may be used in amounts such that 0 to 100%, generally 1 to 90% (if present) of the surface functional groups (Si—OH groups) of the silica nanoparticles are functionalized. The number of functional groups is experimentally determined where quantities of nanoparticles are reacted with an excess of surface modifying agent so that all available reactive sites are functionalized with a surface modifying agent. Lower percentages of functionalization may then be calculated from the result. Generally, the amount of surface modifying agent is used in amount sufficient to provide up to twice the equal weight of surface modifying agent relative to the weight of inorganic nanoparticles. If surface-modified silica nanoparticles are desired, it is preferred to modify the nanoparticles prior to incorporation into the coating composition. The amount of surface modifying agents will vary by the specific filler, size thereof and desired degree of functionalization. If surface-modified silica nanoparticles are desired, it is preferred to modify the nanoparticles prior to incorporation into the coating composition.

In some preferred embodiments, the fillers, particularly the silica fillers, may be surface modified with the addition-fragmentation agent of Formula I. Thus the present disclosure provides addition-fragmentation monomer-modified filler particles. These surface modified filler particles may be compounded with the polymerizable mixture and cured as described herein, with the result that the filler particles are integrated into the cured composition. With reference to Formula I, the surface-modified particle filler may be illustrated as:

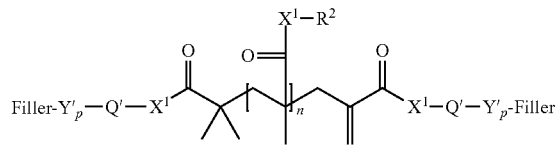

where
Filler is an inorganic filler particle,
$R^2$ is $Y_p$-Q'-, a (hetero)alkyl group or a (hetero)aryl group;
Q' is a covalent bond or an or a linking group, preferably an organic (hetero)hydrocarbyl linking group having a valence of p+1;
Y' is the residue of the surface-binding organic functional group that associates with a substrate on which the addition-fragmentation agent is disposed;
p is 1 or 2;
$X^1$ is independently —O— or —$NR^4$—, where $R^4$ is H or $C_1-C_4$ alkyl, and
n is 0 or 1.

It will be understood in the above Formula that the $R^1$ and $R^3$ groups of formula I were chosen with the "Y-Q'-" surface binding group and that $R^2$ could be so illustrated. It will be further understood that each of $R^1$, $R^2$ and $R^3$ may contain a $Y_p$-Q'- group and that each can contain one or more Y groups.

As used herein the term "residue" is used to define that portion of a functional group remaining after reaction of the functional group with the surface of the inorganic particulate For example, the "residue" of a silane functional group Y of the formula —$SiR^7_3$, would be —O—$Si(R^7)_2$—.

For further illustration, the particular filler may be selected from silica (or a silica composite), and the surface-binding organic functional group "Y" may be selected from a silyl group of the formula —$SiR^7_3$, wherein each $R^7$ group is independently selected from the group of alkoxy, acetoxy, and halide. This would result in a covalent bond between the silica particle and the addition-fragmentation agent illustrated by a Silica-O—$Si(R^7)_2$-linkage. It will be understood that the silyl moiety may form one (as illustrated) or more siloxane bonds with a silica particle or siloxane bonds with othyl sily groups. With reference to formula I, one may selected Y=hydroxamic acid or N-hydroxyurea that may bond to zirconia, a filler used in high index coatings/films as well as in dental composites, Y=phosphates and phosphonates would also be useful for alumina fillers, and Y=thiols for gold.

In general, all or a part of the surface functional groups of an inorganic filler particle may be so modified by the addition-fragmentation agent of Formula I. The fillers may be unmodified, surface modified by surface-modifying agents, surface-modifying agent of Formula I, or a mixture of surface-modifying agents and those of Formula I. Preferably, the addition-fragmentation agent is used in amounts of 0.5 to 30 wt. %, preferably 10-25 wt. %, relative to the weight of the filler particles.

In some embodiments, a combination of surface modifying agents can be useful, wherein at least one of the agents has a functional group co-polymerizable with a curable resin. Other surface modifying agents which do not generally react with curable resins can be included to enhance dispersibility or rheological properties. Examples of silanes of this type include, for example, aryl polyethers, alkyl, hydroxy alkyl, hydroxy aryl, or amino alkyl functional silanes.

The surface modification can be done either subsequent to mixing with the monomers during or after mixing. It is typically preferred to combine the organosilane surface treatment compounds with nanoparticles before incorporation into the resin. The required amount of surface modifier is dependent upon several factors such as particle size, particle type, modifier molecular weight, and modifier type. In some embodiments a monolayer of modifier is attached to the surface of the particle.

The surface modified nanoparticles can be substantially fully crystalline. Fully crystalline nanoparticles (with the exception of silica) typically have a degree of crystallinity (measured as isolated metal oxide particles) greater than 55%, preferably greater than 60%, and more preferably greater than 70%. For example, the degree of crystallinity can range up to about 86% or greater. The degree of crystallinity can be determined by X-ray diffraction techniques. Crystalline (e.g. zirconia) nanoparticles have a high refractive index whereas amorphous nanoparticles typically have a lower refractive index.

In some embodiments, the disclosure provides a universal restorative composite comprising:
a) 15-30 wt % of a curable dental resin comprising at least two polymerizable, ethylenically unsaturated groups;
b) 70-85 wt % of an inorganic filler, preferably a surface modified filler;
c) 0.1 to 10 parts by weight of the addition-fragmentation agent, relative to 100 parts by weight of a) and b), said curable composition further comprising an initiator and <2%, stabilizers, pigments, etc.

In some embodiments, the disclosure provides a flowable restorative (flowable) composite comprising:
a) 25-50 wt % of a curable dental resin comprising at least two polymerizable, ethylenically unsaturated groups;
b) 50-75 wt % of an inorganic filler, preferably a surface modified filler;
c) 0.1 to 10 parts by weight of the addition-fragmentation agent, relative to 100 parts by weight of a) and b), said curable composition further comprising an initiator and <2% initiators, stabilizers, pigments, etc.

In some embodiments, the disclosure provides a resin modified glass-ionomer adhesive comprising:
a) 10-25 wt. % of a partially (meth)acrylated poly(meth) acrylic acid;
b) 5-20% of a hydroxyalkyl (meth)acrylate;
c) 30-60% of fluoroaluminosilicate (FAS) acid reactive glass
d) 0-20% non-acid reactive fillers, preferably surface-treated;
e) 10-20% water; and
f) 0.1 to 10 wt. % of the addition-fragmentation agent, relative to 100 parts by weight of a) and b)),
g) said curable composition further comprising an initiator and <2% stabilizers, pigments, etc.

Preferably the floroaluminosilicate is a silane methacrylate surface-treated floroaluminosilicate.

In some embodiments, the disclosure provides a dental adhesive comprising:
a) 30-8-wt. % mono(meth)acrylate) monomers;
b) 1-10 wt. % polyfunctional (meth)acrylate monomers;
c) 5-60 wt. %% monomers having a acid-functional group (including phosphate, phosphonate, carboxylate, sulfonic acids)
d) 0-10, preferably 1-10 wt. % poly(meth)acrylic acid methacrylate monomers;
e) 0.1 to 10 wt. % of the addition-fragmentation agent, relative to 100 parts by weight of a) to d);
f) an initiator,
g) 0-30% inorganic filler, preferably surface modified, relative to 100 parts by weight of a) to d);
h) 0 to 25 wt. % solvent relative to 100 parts by weight of a) to d);
i) 0 to 25 wt. % water relative to 100 parts by weight of a) to d); and
<2% stabilizers, pigments, etc.

In some embodiments, the dental compositions can have an initial color different than the cured dental structures. Color can be imparted to the composition through the use of a photobleachable or thermochromic dye. As used herein, "photobleachable" refers to loss of color upon exposure to actinic radiation. The composition can include at least 0.001 wt-% photobleachable or thermochromic dye, and typically at least 0.002 wt-% photobleachable or thermochromic dye, based on the total weight of the composition. The composition typically includes at most 1 wt-% photobleachable or thermochromic dye, and more typically at most 0.1 wt-% photobleachable or thermochromic dye, based on the total weight of the composition. The amount of photobleachable and/or thermochromic dye may vary depending on its extinction coefficient, the ability of the human eye to discern the initial color, and the desired color change. Suitable thermochromic dyes are disclosed, for example, in U.S. Pat. No. 6,670,436 (Burgath et al.).

For embodiments including a photobleachable dye, the color formation and bleaching characteristics of the photobleachable dye varies depending on a variety of factors including, for example, acid strength, dielectric constant, polarity, amount of oxygen, and moisture content in the atmosphere. However, the bleaching properties of the dye can be readily determined by irradiating the composition and evaluating the change in color. The photobleachable dye is generally at least partially soluble in a hardenable resin.

Photobleachable dyes include, for example, Rose Bengal, Methylene Violet, Methylene Blue, Fluorescein, Eosin Yellow, Eosin Y, Ethyl Eosin, Eosin bluish, Eosin B, Erythrosin B, Erythrosin Yellowish Blend, Toluidine Blue, 4',5'-Dibromofluorescein, and combinations thereof.

The color change can be initiated by actinic radiation such as provided by a dental curing light which emits visible or near infrared (IR) light for a sufficient amount of time. The mechanism that initiates the color change in the compositions may be separate from or substantially simultaneous with the hardening mechanism that hardens the resin. For example, a composition may harden when polymerization is initiated chemically (e.g., redox initiation) or thermally, and the color change from an initial color to a final color may occur subsequent to the hardening process upon exposure to actinic radiation.

Optionally, compositions may contain solvents (e.g., alcohols (e.g., propanol, ethanol), ketones (e.g., acetone, methyl ethyl ketone), esters (e.g., ethyl acetate), other nonaqueous solvents (e.g., dimethylformamide, dimethylacetamide, dimethylsulfoxide, 1-methyl-2-pyrrolidinone)), and water.

If desired, the compositions can contain additives such as indicators, dyes, pigments, inhibitors, accelerators, viscosity modifiers, wetting agents, buffering agents, radical and cationic stabilizers (for example BHT), and other similar ingredients that will be apparent to those skilled in the art.

Additionally, medicaments or other therapeutic substances can be optionally added to the dental compositions. Examples include, but are not limited to, fluoride sources, whitening agents, anticaries agents (e.g., xylitol), calcium sources, phosphorus sources, remineralizing agents (e.g., calcium phosphate compounds), enzymes, breath fresheners, anesthetics, clotting agents, acid neutralizers, chemotherapeutic agents, immune response modifiers, thixotropes, polyols, anti-inflammatory agents, antimicrobial agents (in addition to the antimicrobial lipid component), antifungal agents, agents for treating xerostomia, desensitizers, and the like, of the type often used in dental compositions. Combinations of any of the above additives may also be employed. The selection and amount of any one such additive can be selected by one of skill in the art to accomplish the desired result without undue experimentation.

The curable dental composition can be used to treat an oral surface such as tooth, as known in the art. In some embodiments, the compositions can be hardened by curing after applying the dental composition. For example, when the curable dental composition is used as a restorative such as a dental filling, the method generally comprises applying the curable composition to an oral surface (e.g. cavity); and curing the composition. In some embodiments, a dental adhesive may be applied prior to application of the curable dental restoration material described herein. Dental adhesives are also typically hardened by curing concurrently with curing the highly filled dental restoration composition. The method of treating an oral surface may comprise providing a dental article and adhering the dental article to an oral (e.g. tooth) surface.

In other embodiments, the compositions can be cured into dental articles prior to applying. For example, a dental article such as a crown may be pre-formed from the curable dental composition described herein. Dental composite (e.g. crowns) articles can be made from the curable composition described herein by casting the curable composition in contact with a mold and curing the composition. Alternatively, dental composites or articles (e.g. crowns) can be made by first curing the composition forming a mill blank and then mechanically milling the composition into the desired article.

Another method of treating a tooth surface comprises providing a dental composition as described herein wherein the composition is in the form of a (partially cured) curable, self-supporting, malleable structure having a first semi-finished shape; placing the curable dental composition on a tooth surface in the mouth of a subject; customizing the shape of the curable dental composition; and hardening the curable dental composition. The customization can occur in the patient's mouth or on a model outside the patient mouth such as described in U.S. Pat. No. 7,674,850 (Karim et al.); incorporated herein by reference.

In some embodiments the addition-fragmentation agent (AFM) per se may serve as a primer whereby the agent is applied to a dental structure surface and binds therewith. In these embodiments a thin layer of the AFM of Formula I may be applied to a dental structure surface and then an additional layer of dental resin applied to the AFM-primed dental structure surface. The specific binding group Y is chosen from those that self-adhere or self-etch and include a monophosphate, a phosphonate, a phosphonic acid, a hydroxamic acid, a carboxylic acid, and acetoacetate, an anhydride, an isonitrile group, a silyl, a disulfide, a thiol, an amino, a sulfinic acid, a sulfonic acid, a phosphine, a phenolic (including catechols and 1,2,3-trihydroxy benzene derivatives), or a heterocyclic aromatic group. Preferred Y groups include a monophosphate, a phosphonate, a phosphonic acid, and a carboxylic acid.

The AFM bound to the dental structure surface may be represented as follows:

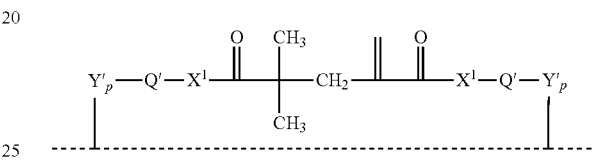

where the dashed line represents the surface of a dental structure, and the bond between the substrate and binding group Y' may be a covalent or ionic bond as described supra. The remaining groups are as previously described for the surface-modified filler particles. As can be seen, such dental structure surfaces are provided with an $\alpha,\beta$-ethylenically unsaturated group that may be copolymerized with dental resins. In particular, the AFM surface modified dental structure may be subsequently coated and cured with the dental resins containing the AFM. It is believed that the ethylenically unsaturated group will be incorporated into the polymerizable composition during curing providing a secure bond between substrate and coating.

Objects and advantages are further illustrated by the following examples, but the particular materials and amounts thereof recited in these examples, as well as other conditions and details, should not be construed to unduly limit this invention. Unless otherwise indicated, all parts and percentages are on a weight basis.

EXAMPLES

As used herein, all parts and percentages are by weight unless otherwise specified. The addition fragmentation agent is referred to in the examples as an addition fragmentation ligand (AFL). All commercial materials were used as obtained from the vendor. Unless otherwise specified, materials can be obtained from Sigma-Aldrich, Milwaukee, Wis.

Test Methods

Diametral Tensile Strength (DTS) Test Method

Diametral tensile strength of a cured composition was measured in this test. An uncured test sample composition was injected into a 4-mm (inside diameter) glass tube and the tube was capped with silicone rubber plugs. The tube was compressed axially at approximately 2.88 kg/cm² pressure for 5 minutes. The sample was then light cured for 80 seconds by exposure to a XL 1500 dental curing light (3M ESPE, St. Paul, Minn.), followed by irradiation for 90 seconds in a Kulzer UniXS curing box (Heraeus Kulzer GmbH, Germany). The test sample was cut with a diamond saw to form disks about 2 mm thick, which were stored in distilled water at 37° C. for about 24 hours prior to testing. Measurements were carried out on an Instron tester (Instron 4505, Instron Corp., Canton, Mass.) with a 10 kilonewton (kN) load cell at a crosshead speed of 1 mm/minute according to ISO Specification 7489 (or American Dental Association (ADA) Specification No. 27). Test results were reported in MPa (megapascals) as the average of multiple measurements.

Stress Test Method (Cusp Deflection)

The Stress Test Method measures the stress development during the curing process of a test sample composition. An 8×2.5×2 mm slot was machined in a rectangular 15×8×8 mm aluminum block to form a test fixture for each test sample. The slot was located 2 mm along an edge, thus forming a 2 mm wide aluminum cusp adjacent to and parallel to the 2 mm wide cavity containing compositions to be tested. A linear variable displacement transducer (Model GT 1000, used with an E309 analog amplifier, both from RDP Electronics, United Kingdom) was positioned so as to measure the displacement of the cusp tip as the composition photocured at room temperature. Prior to testing, the slot in the aluminum block was sandblasted using Rocatec Plus Special Surface Coating Blasting Material (3M ESPE, St. Paul, Minn.), treated with RelyX Ceramic Primer (3M ESPE), and finally treated with a dental adhesive, Adper Easy Bond (3M ESPE). The slot was fully packed with approximately 100 mg of the sample compositions. The material was irradiated for 1 minute with a dental curing lamp (Elipar S-10, 3M ESPE) positioned almost in contact (<1 mm) with the material in the slot, then the displacement of the cusp in microns was recorded 9 minutes after the lamp was extinguished.

Materials

2-Mercaptoethanol—Alfa Aesar, Ward Hill, Mass., USA
3-chloro-2-chloromethyl-1-propene—Secant Chemicals, Inc., USA
3-triethoxysilylpropyl isocyanate—Sigma Aldrich, St. Louis, Mo., USA
BHT—butylated hydroxytoluene, Sigma-Aldrich, Milwaukee, Wis., USA
Cobalt(II) acetate tetrahydrate—Alfa Aesar, Ward Hill, Mass., USA
CPQ—camphorquinone, Sigma-Alrich
DDDMA—dodecanedioldimethacrylate, Sartomer
Dibutyltin dilaurate—Alfa Aesar, Ward Hill, Mass., USA
Dimethyl glyoxime—Alfa Aesar, Ward Hill, Mass., USA
DI water—deionized water
Diol 2—diol prepared as described in U.S. Patent Publication No. 2012/0208965 under Example 2—Preparation of AFM-2 via Diol 2.
DPIHFP—Diphenyliodonium hexafluorophosphate (≥98%), Sigma-Aldrich
ENMAP—ethyl N-methyl-N-phenyl-3-aminopropionate, CAS No. 2003-76-1; this is the compound of Formula 1-a in U.S. Pat. Appl. No. 2010-0311858 (Holmes) The compound may be synthesized by the methods described by Adamson, et al., JCSOA9; J. Chem. Soc.; 1949; spl. 144,152, which is incorporated herein by reference.
ERGP-IEM—prepared as described in the Example section of EP Patent Publication Number EP 2401998
Ethanol—Pharmaco-AAPER, Brookfield, Conn., USA
Ethyl acetate—EMD Chemicals Inc., Gibbstown, N.J., USA
GF-31 Silane—3-Methacryloxypropyltrimethoxysilane, Wacker Chemie AG, Munich, Germany; Silquest A-174, Momentive Performance Materials; Albany, N.Y., also used
HEMA—2-Hydroxyethyl methacrylate, Sigma-Aldrich
$NH_4OH$ solution—Ammonium hydroxide solution, 30% $NH_4OH$ in water—Sigma Aldrich
Nanozirconia filler—silane-treated nanozirconia powder was prepared as described in U.S. Pat. No. 7,156,911, Preparatory Example 1A except that GF-31 silane was used instead of SILQUEST A-1230. The GF-31 silane was charged at approximately 1.2 millimole silane/g oxide.
Nanosilica filler (also referred to as 20 nm silica)—silane-treated nanosilica powder, with a nominal particle size of 20 nm; prepared as described in U.S. Pat. No. 6,572,693 (column 21, lines 63-67 for nanosized particle filler, Type #2)
Particle A (125 $m^2/g$ silica/zirconia nanocluster)—aggregated particle cluster material prepared as described generally in U.S. Pat. No. 6,730,156, Preparatory Example A. The material had a surface area of 125 $m^2/g$, and a weight ratio of silica/zirconia of 73/27. Preparation of the material is more specifically described in U.S. Patent application No. 20110196062, Fillers and Composite Materials with Zirconia and Silica Nanoparticles, (Bradley) paragraphs [0067]-[0073], filed Oct. 9, 2009, and references therein (namely, U.S. Pat. No. 6,376,590 (Kolb, et al.), filed on Oct. 28, 1999, or U.S. Pat. No. 7,429,422 (Davidson et al.), filed Jun. 7, 2007,) each of which is hereby incorporated by reference.
Pyridine—Alfa Aesar, Heysham, Lanc, England
UDMA—Rohamere™ 6661-0 (diurethane dimethacrylate, CAS No. 41 137-60-4), Rohm Tech, Inc., Malden, Mass.
$YbF_3$—Ytterbium fluoride, 100 nanometer particle size; Sukgyung, Korea Preparatory Example P1

Diol 1

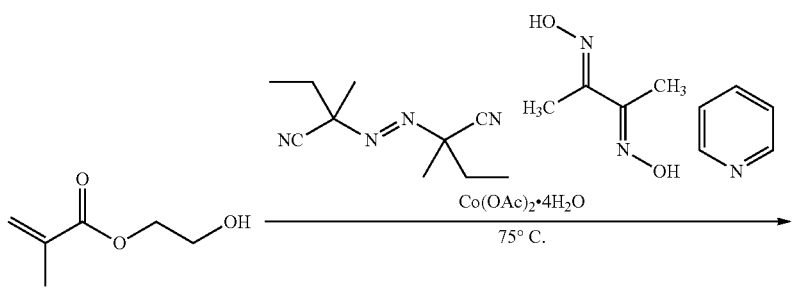

-continued

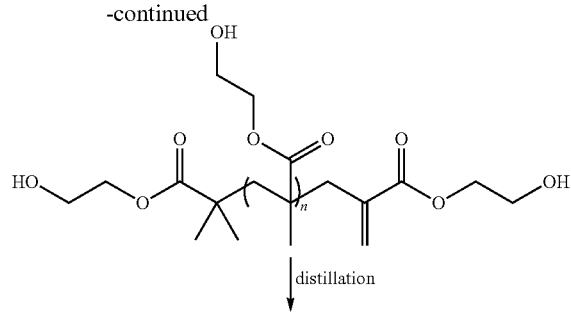

↓ distillation

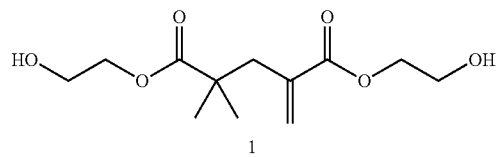

1

An oven-dried, three-neck 250 mL round-bottomed flask was equipped with a magnetic stir bar, gas inlet adapter, and 250 mL pressure-equalizing addition funnel capped with a rubber septum, and a rubber septum. The apparatus was allowed to cool to room temperature under nitrogen. HEMA (100 mL, 107.3 g, 824.5 mmol) and Vazo™ 67 (0.215 g, 1.12 mmol) were added to the reaction flask and the mixture was stirred. The addition funnel was charged with HEMA (200 mL, 214.6 g, 1649 mmol) and Vazo™ 67 (0.430 g, 2.24 mmol). The solutions of Vazo™ 67 in HEMA were sparged with nitrogen for 30 minutes after which the reaction was maintained under nitrogen. Then cobalt(II) acetate tetrahydrate (0.104 g, 0.418 mmol), dimethyl glyoxime (0.158 g, 1.36), and pyridine (0.250 mL, 0.245 g, 3.10 mmol) were added to the pot and stirred while heating to 75° C. in an oil bath. The solution of HEMA and Vazo™ 67 were added to the pot dropwise over 1.5 hours. After an additional hour, Vazo™ 67 (0.0164 g, 0.0853 mmol) was added to the pot. The reaction was allowed to stir at 75° C. for an additional 18 hours and then allowed to cool to room temperature. The dimer product was distilled from the reaction mixture using a short-path distillation apparatus. The dimer distilled at approximately 140° C. at a pressure of 0.09 mm Hg. A colorless, clear viscous liquid was obtained (136.2 g). 50 g of the distilled product was dissolved in ethyl acetate (250 mL) and washed with deionized water (3×125 mL). The ethyl acetate solution was dried over sodium sulfate for 30 minutes and then vacuum filtered to remove the drying agent. The ethyl acetate solution was concentrated in vacuo to provide Diol 1 (26.13 g).

Example 1

AFL-1

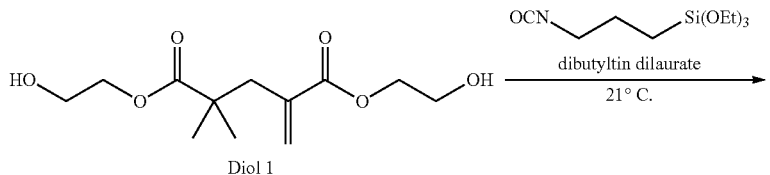

Diol 1

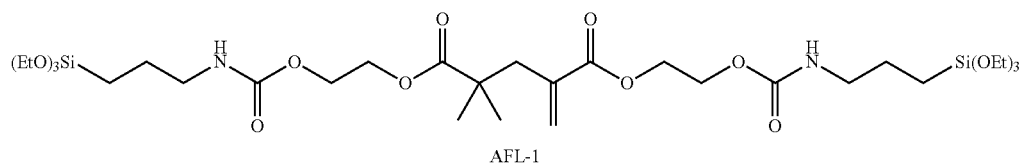

AFL-1

A 40 mL amber bottle was charged with Diol 1 (7.500 g, 28.82 mmol) and 3-isocyanatopropyl triethoxysilane (14.255 g, 57.63 mmol). A magnetic stir bar was added to the bottle. With stirring, dibutyltin dilaurate (2 drops from the tip of a glass pipette) was added and the reaction was sealed with a Teflon-lined plastic cap. After 3 days, the reaction was sampled, and $^1$H NMR analysis was consistent with the desired product, AFL-1. AFL-1 (21.73 g, 28.79 mmol, 99.9%) was obtained as a colorless, clear viscous material.

Example 2

AFL-2

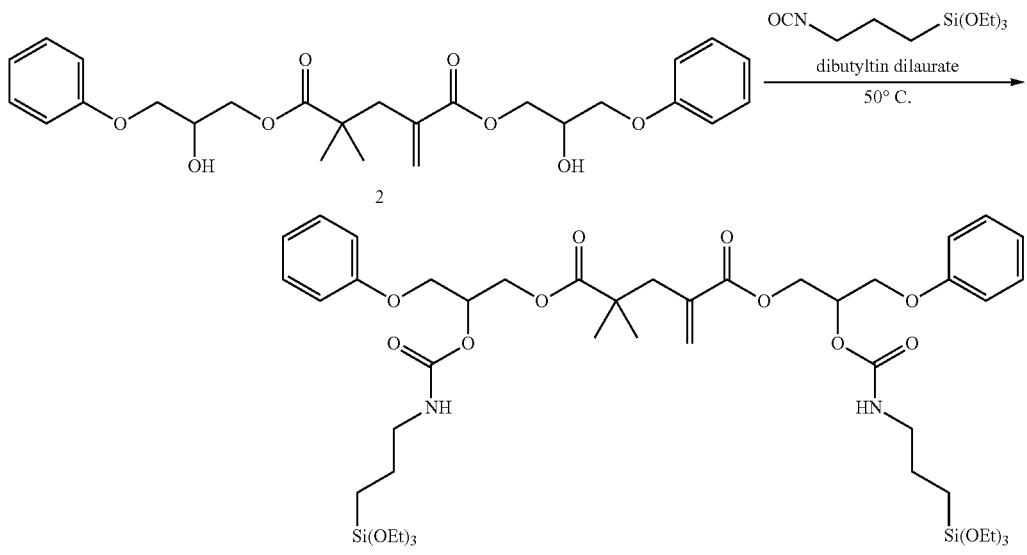

AFL-2

A 40 mL amber bottle was charged with Diol 2 (10.00 g, 21.16 mmol) and 3-isocyanatopropyl triethoxysilane (10.47 g, 42.33 mmol). A magnetic stir bar was added to the bottle. With stirring, dibutyltin dilaurate (2 drops from the tip of a glass pipette) was added and the reaction was sealed with a Teflon-lined plastic cap. The reaction mixture was heated to 50° C. with stirring. After 2 days, the reaction was cooled to room temperature and sampled. $^1$H NMR analysis was consistent with the desired product, AFL-2. AFL-2 (20.33 g, 21.02 mmol, 99.3%) was obtained as a very pale yellow, clear viscous material.

Example 3

AFL-3

A solution was prepared by dissolving 2-Mercaptoethanol (25.60 g, 0.328 mol) in 100 mL of ethanol in a 500 mL 2-neck round-bottom flask equipped with a magnetic stirring bar, condenser and a dropping funnel. With vigorous stirring, sodium metal (8.20 g, 0.356 mol) was added in small pieces slowly to control the exotherm during addition. After complete addition of the sodium metal, the mixture was stirred under a nitrogen blanket until the flask contents cooled to room temperature. A solution of 3-chloro-2-chloromethyl-1-propene ((20 g, 0.16 mol) in 50 mL of ethanol) was added dropwise using the dropping funnel to form a white cloudy mixture then a heterogeneous mixture with a white solid after all of the dichloro propene component was added. The flask contents were refluxed for 45 minutes then cooled to room temperature. The white solid was removed by vacuum filtration and the filter cake was washed with excess ethanol on top of the original filtrate. The solvent was removed in a rotary evaporator followed by drying in a vacuum pump to provide a colorless liquid. The crude product was distilled under vacuum (6-7 torr) and 135-150 C to provide the desired product, 2-methylenepropane-1,3-bis(2-hydroxyethyl sulfide, with 75-80% recovery.

A mixture was prepared by charging 2-methylenepropane-1,3-bis(2-hydroxyethyl sulfide) (7.0 g, 0.034 mol), 3-triethoxysilylpropyl isocyanate (16.60 g, 0.067 mol), BHT (0.016 g) and dibutyltin dilaurate catalyst (3 drops) into a 100 mL glass jar. The jar was swirled by hand for two minutes during which the mixture started to blend and react. The mixture became clear in color with some exotherm. The jar

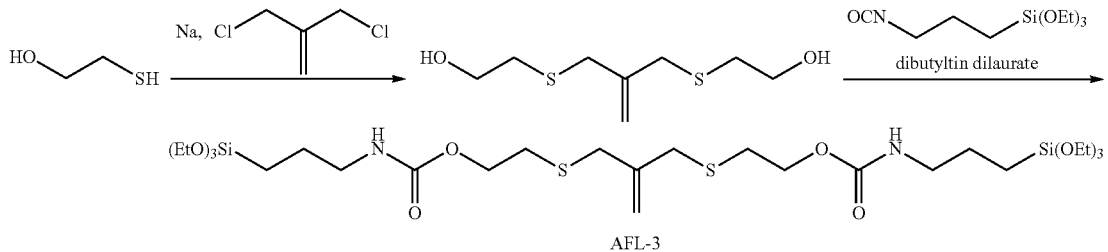

AFL-3 was left to cool to room temperature. IR spectrum showed complete disappearance of the NCO band (~2200-2400 cm-1). NMR was recorded and found to be consistent with the desired structure of AFL-3. The reaction yield was quantitative.

Examples 4-5

Control Example C1—Functionalized Fillers

In Example 4, a functionalized filler was prepared by mixing 10 g of Particle A, 1.0502 g of AFL-1, 10.64 g of ethyl acetate, and 0.21 g of a NH$_4$OH solution, and stirring overnight at room temperature. The mixture was then flash dried and then dried in an oven for 30 minutes at 80° C.

In Example 5, a functionalized filler was prepared as in Example 4 except that the composition was 10 grams of Particle A, 1.055 g of AFL-3, 0.944 g GF-31 silane, 10.473 g of ethyl acetate and 0.203 g of NH$_4$OH solution.

Control Example C1 was prepared as in Example 4 except that the composition was 10 g of Particle A, 2.0999 g of GF-31 silane, 20.5632 g of ethyl acetate, and 0.4002 g of NH$_4$OH solution.

Examples 6-7

Control Example C2—Resins

A resin composition was prepared by hand mixing the composition shown in Table 1 to form a uniform mixture.

TABLE 1

Resin Composition

| Component | Weight - grams |
|---|---|
| UDMA Resin | 2.1508 |
| CPQ | 0.0644 |
| DPIHFP | 0.0603 |
| ENMAP | 0.3028 |
| BHT | 0.0304 |
| DDDMA | 0.586 |
| ERGP-IEM | 16.9098 |

In Example 6, a paste suitable for dental resins was prepared by mixing 2.675 g of the resin mixture, 0.5493 g of YbF$_3$, 0.2855 g of Nanosilica filler, 0.1536 g of Nanozirconia filler, 0.0669 g of the filler from Example 4, and 6.2269 g of the filler from Example C1 with a speed mixer.

Example 7 was prepared as in Example 6 except the composition was 2.675 g of resin, 0.5497 g of YbF$_3$, 0.2862 g of Nanosilica filler, 0.1539 g of nanozirconia filler, and 6.3361 g of the filler from Example 5.

Control Example C2 was prepared as in Example 7 except that the filler from Example C1 was used.

The adhesives were tested for diametral strength (DTS) and stress (Cusp Deflection) according to the above test methods. Results are shown in Table 2.

TABLE 2

| Example | GF-31 Silane (Wt %) | AFL Ex 4 (Wt %) | AFL Ex 5 (Wt %) | DTS (MPa) | Cusp Deflection (micrometers) |
|---|---|---|---|---|---|
| 6 | 90 | 10 | 0 | 82.32 | 3.13 |
| 7 | 90 | 0 | 10 | 80.73 | 2.54 |
| C2 | 100 | 0 | 0 | 85.08 | 3.31 |

The invention claimed is:

1. A curable dental composition comprising:
   a) at least one dental resin comprising at least two ethylenically unsaturated groups;
   b) an addition-fragmentation agent comprising:
      1) a labile addition-fragmentation group; and
      2) at least two surface-binding functional groups; and
   c) optionally an inorganic oxide filler,
   wherein the addition-fragmentation agent is of the formula:

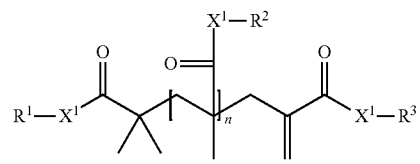

wherein
   R$^1$, R$^2$ and R$^3$ are each independently Y-Q'-, a (hetero)alkyl group or a (hetero)aryl group with the proviso that at least two of R', R$^2$ and R$^3$ is Y$_p$-Q'-
   Q' is a covalent bond or a linking group having a valence of p+1;
   Y is a surface-binding organic functional group;
   p is 1 or 2;
   X$^1$ is independently —O— or —NR$^4$—, where R$^4$ is H or C$_1$-C$_4$ alkyl, and
   n is 0 or 1
   wherein
   Y-Q' is selected from a monophosphate, a phosphonate group, a phosphonic acid group, a hydroxamic acid group, a carboxylic acid group, and acetoacetate group, an anhydride group, an isonitrile group, a silyl group, a disulfide group, a thiol group, an amino group, a sulfinic acid group, a sulfonic acid group, a phosphine group, a phenolic group or a heterocyclic aromatic group.

2. The dental composition of claim 1 wherein Q' is selected from —O—, —S—, —N(R$^4$)—, —SO$_2$—, —PO$_2$—, —CO—, —OCO—, —R$^6$—, —N(R$^4$)—CO—N(R$^4$)—, —N(R$^4$)—CO—O—, —N(R$^4$)—CO—N(R$^4$)—CO—O—R$^6$—, —CO—N(R$^4$)—R$^6$—, —R$^6$—CO—O—R$^6$—, —O—R$^6$—, —S—R$^6$—, —N(R$^4$)—R$^6$—, —SO$_2$—R$^6$—, —PO$_2$—R$^6$—, —CO—R$^6$—, —OCO—R$^6$—, —N(R$^4$)—CO—R$^6$—, —N(R$^4$)—R$^6$—CO—O—, and —N(R$^4$)—CO—N(R$^4$)—, wherein each R$^4$ is hydrogen, a C$_1$ to C$_4$ alkyl group, or aryl group, each R$^6$ is an alkylene group having 1 to 6 carbon atoms, a 5- or 6-membered cycloalkylene group having 5 to 10 carbon atoms, or a divalent arylene group having 6 to 16 carbon atoms, with the proviso that Q-Z does not contain peroxidic linkages.

3. The dental composition of claim 1 wherein Q' is an alkylene of the formula —C$_r$H$_{2r}$—, where r is 1 to 10.

4. The dental composition of claim 1 wherein Q' is a hydroxyl-substituted alkylene of the formula —CH$_2$—CH(OH)—CH$_2$—.

5. The dental composition of claim 1 wherein Q' is an aryloxy-substituted alkylene, or an alkoxy-substituted alkylene.

6. The dental composition of claim 1 wherein the ethylenically unsaturated groups of the dental resin are (meth)acrylate groups.

7. The dental composition of claim 1 wherein the dental resin comprises an aromatic monomer having a refractive index of at least 1.50.

8. The dental composition of claim 1 wherein the dental resin is a low volume shrinkage resin.

9. The dental composition of claim 1 wherein the dental resin is an isocyanurate resin, a tricyclodecane resin, cyclic allylic sulfide resins; methylene dithiepane silane resins; and poly(meth)acryloyl-containing resins, or mixtures thereof.

10. The dental composition of claim 1 wherein the dental composition further comprises at least one other (meth)acrylate monomer is selected from the group consisting of ethoxylated bisphenol A dimethacrylate, 2-hydroxyethyl methacrylate, bisphenol A diglycidyl dimethacrylate, urethane dimethacrylate, triethlyene glycol dimethacrylate, glycerol dimethacrylate, ethylenegylcol dimethacrylate, neopentylglycol dimethacrylate (NPGDMA), polyethyleneglycol dimethacrylate, and mixtures thereof.

11. The dental composition of claim 1 wherein the inorganic oxide filler comprises nanoparticles.

12. The dental composition of claim 1 comprising a surface modified inorganic oxide filler.

13. A method of treating a tooth surface, the method comprising
   a) providing a curable dental resin of claim 1;
   b) placing the dental composition on a tooth surface in the mouth of a subject; and
   c) hardening the hardenable dental composition.

14. The curable dental composition of claim 1 comprising a universal dental restorative comprising:
   a) 15-30 wt % of a curable dental resin comprising at least two polymerizable, ethylenically unsaturated groups;
   b) 70-85 wt % of an inorganic filler;
   c) 0.1 to 10 parts by weight of the addition-fragmentation agent, relative to 100 parts by weight of a) and b),
   said curable composition further comprising an initiator and;
   <2% of stabilizers and pigments.

15. The curable dental composition of claim 1 comprising a flowable restorative composite comprising:
   a) 25-50 wt % of a curable dental resin comprising at least two polymerizable, ethylenically unsaturated groups;
   b) 50-75 wt % of an inorganic filler;
   c) 0.1 to 10 parts by weight of the addition-fragmentation agent relative to 100 parts by weight of a) and b);
   d) an initiator;
   e) <2% stabilizers and pigments,
   f) optionally 5-60 wt. % monomers having an acid-functional group; and
   g) an initiator.

16. The curable dental composition of claim 1 comprising a resin-modified glass-ionomer adhesive comprising:
   a) 10-25 wt. % of a partially (meth)acrylated poly(meth)acrylic acid;
   b) 5-20% of a hydroxyalkyl (meth)acrylate;
   c) 30-60% of fluoroaluminosilicate (FAS) acid reactive glass;
   d) 0-20% non-acid reactive fillers;
   e) 10-20% water;
   f) 0.1 to 10 wt. % of the addition-fragmentation agent, relative to 100 parts by weight of a) and b); and
   g) an initiator.

17. The curable dental composition of claim 1 further comprising a surface-modified inorganic filler of the formula:

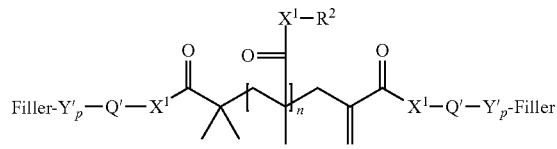

where
Filler is an inorganic filler particle,
$R^2$ is $Y_p$-Q'-, a (hetero)alkyl group or a (hetero)aryl group;
Q' is a covalent bond or an organic (hetero)hydrocarbyl linking group having a valence of p+1;
Y' is the residue of the surface-binding functional group Y;
p is 1 or 2;
$X^1$ is independently —O— or —NR$^4$—, where $R^4$ is H or $C_1$-$C_4$ alkyl, and
n is 0 or 1.

18. The curable dental composition of claim 17 wherein the Filler is silica.

19. The curable dental composition of claim 17 wherein the group Filler-Y'$_p$— is of the formula Silica-O—Si(R$^7$)$_2$— wherein each $R^7$ group is independently selected from the group of alkoxy, acetoxy, and halide.

* * * * *